United States Patent
Park et al.

(10) Patent No.: US 10,582,934 B2
(45) Date of Patent: Mar. 10, 2020

(54) GENERATING MRI IMAGES USABLE FOR THE CREATION OF 3D BONE MODELS EMPLOYED TO MAKE CUSTOMIZED ARTHROPLASTY JIGS

(75) Inventors: Ilwhan Park, Walnut Creek, CA (US); Stephen M. Howell, Elk Grove, CA (US)

(73) Assignee: Howmedica Osteonics Corporation, Mahwah, NJ (US)

(*) Notice: Subject to any disclaimer, the term of this patent is extended or adjusted under 35 U.S.C. 154(b) by 2232 days.

(21) Appl. No.: 11/946,002

(22) Filed: Nov. 27, 2007

(65) Prior Publication Data

US 2009/0138020 A1 May 28, 2009

(51) Int. Cl.
*A61B 5/05* (2006.01)
*A61B 17/15* (2006.01)
(Continued)

(52) U.S. Cl.
CPC ............ *A61B 17/154* (2013.01); *A61B 5/055* (2013.01); *A61B 5/4528* (2013.01); *A61B 34/10* (2016.02);
(Continued)

(58) Field of Classification Search
CPC ... A61B 17/154; A61B 17/155; A61B 17/157; A61B 2034/105; A61B 2090/374; A61B 34/10; A61B 5/055; A61B 5/4528
(Continued)

(56) References Cited

U.S. PATENT DOCUMENTS

| | | |
|---|---|---|
| 3,195,411 A | 7/1965 | MacDonald et al. |
| 3,825,151 A | 7/1974 | Arnaud |

(Continued)

FOREIGN PATENT DOCUMENTS

| | | |
|---|---|---|
| DE | 3305237 | 2/1983 |
| DE | 4341367 C1 | 6/1995 |

(Continued)

OTHER PUBLICATIONS

Siemens MAGNETOM Sonata 1.5T Technical Specifications, pp. 1-4, accessed online Jan. 28, 2014.*

(Continued)

*Primary Examiner* — Christopher L Cook
(74) *Attorney, Agent, or Firm* — Polsinelli PC

(57) ABSTRACT

Disclosed herein is a method of creating a customized arthroplasty jig. The method may include: generating two-dimensional MRI images of a patient's joint area to undergo arthroplasty; electronically orienting the two dimensional MRI image slices to account for the patient's joint area being randomly physically oriented in a scanning area of a MRI machine; generating a three-dimensional bone image of at least a portion of a bone of the patient's joint area from the generated two-dimensional MRI images; using the three-dimensional bone image to generate data pertaining to the customized arthroplasty jig, wherein the data includes bone surface information; providing the data to at least one manufacturing device; and employing the bone surface information to cause the at least one manufacturing device to create a surface on the arthroplasty jig configured to matingly receive a surface of the bone.

2 Claims, 16 Drawing Sheets

(51) Int. Cl.
*A61B 5/00* (2006.01)
*A61B 5/055* (2006.01)
*A61B 34/10* (2016.01)
*A61B 90/00* (2016.01)

(52) U.S. Cl.
CPC ........... *A61B 17/155* (2013.01); *A61B 17/157* (2013.01); *A61B 2034/105* (2016.02); *A61B 2090/374* (2016.02)

(58) Field of Classification Search
USPC ................ 600/410, 416, 425; 382/128, 130; 345/419, 629, 630
See application file for complete search history.

(56) References Cited

U.S. PATENT DOCUMENTS

| | | |
|---|---|---|
| D245,920 S | 9/1977 | Shen |
| 4,198,712 A | 4/1980 | Swanson |
| 4,298,992 A | 11/1981 | Burstein |
| 4,436,684 A | 3/1984 | White |
| D274,093 S | 5/1984 | Kenna |
| D274,161 S | 6/1984 | Kenna |
| 4,467,801 A | 8/1984 | Whiteside |
| 4,517,969 A | 5/1985 | Halcomb et al. |
| 4,575,330 A | 3/1986 | Hull |
| 4,646,726 A | 3/1987 | Westin et al. |
| 4,719,585 A | 1/1988 | Cline et al. |
| 4,721,104 A | 1/1988 | Kaufman et al. |
| 4,821,213 A | 4/1989 | Cline et al. |
| 4,822,365 A | 4/1989 | Walker et al. |
| 4,825,857 A | 5/1989 | Kenna |
| 4,841,975 A | 6/1989 | Woolson |
| 4,931,056 A | 6/1990 | Ghajar et al. |
| 4,936,862 A | 6/1990 | Walker et al. |
| 4,976,737 A | 12/1990 | Leake |
| 5,007,936 A | 4/1991 | Woolson |
| 5,011,405 A | 4/1991 | Lemchen |
| 5,027,281 A | 6/1991 | Rekow et al. |
| 5,030,219 A | 7/1991 | Matsen, III et al. |
| 5,035,699 A | 7/1991 | Coates |
| 5,037,424 A | 8/1991 | Aboczsky |
| 5,075,866 A | 12/1991 | Goto et al. |
| 5,078,719 A | 1/1992 | Schreiber |
| 5,086,401 A | 2/1992 | Glassman et al. |
| 5,098,383 A | 3/1992 | Hemmy et al. |
| 5,098,436 A | 3/1992 | Ferrante et al. |
| 5,099,846 A | 3/1992 | Hardy |
| 5,122,144 A | 6/1992 | Bert et al. |
| 5,123,927 A | 6/1992 | Duncan et al. |
| 5,133,758 A * | 7/1992 | Hollister .................. A61F 2/38 623/20.31 |
| 5,139,419 A | 8/1992 | Andreiko et al. |
| 5,140,646 A | 8/1992 | Ueda |
| 5,141,512 A | 8/1992 | Farmer et al. |
| 5,154,717 A | 10/1992 | Matsen, III et al. |
| 5,156,777 A | 10/1992 | Kaye |
| 5,171,276 A | 12/1992 | Caspari et al. |
| D336,518 S | 6/1993 | Taylor |
| 5,218,427 A | 6/1993 | Koch |
| 5,234,433 A | 8/1993 | Bert et al. |
| 5,236,461 A | 8/1993 | Forte |
| 5,274,565 A | 12/1993 | Reuben |
| 5,282,803 A | 2/1994 | Lackey |
| 5,298,115 A | 3/1994 | Leonard |
| 5,298,254 A | 3/1994 | Prewett et al. |
| 5,305,203 A | 4/1994 | Raab |
| D346,979 S | 5/1994 | Stalcup et al. |
| 5,320,529 A | 6/1994 | Pompa |
| 5,360,446 A | 11/1994 | Kennedy |
| 5,364,402 A | 11/1994 | Mumme et al. |
| 5,365,996 A | 11/1994 | Crook |
| 5,368,478 A | 11/1994 | Andreiko et al. |
| D355,254 S | 2/1995 | Krafft et al. |
| D357,315 S | 4/1995 | Dietz |
| 5,408,409 A | 4/1995 | Glassman et al. |
| 5,431,562 A | 7/1995 | Andreiko et al. |
| 5,448,489 A | 9/1995 | Reuben |
| 5,452,407 A | 9/1995 | Crook |
| 5,454,717 A | 10/1995 | Andreiko |
| 5,462,550 A | 10/1995 | Dietz et al. |
| 5,484,446 A | 1/1996 | Burke et al. |
| 5,514,140 A | 5/1996 | Lackey |
| D372,309 S | 7/1996 | Heldreth |
| D374,078 S | 9/1996 | Johnson et al. |
| 5,556,278 A | 9/1996 | Meitner |
| 5,569,260 A | 10/1996 | Petersen |
| 5,569,261 A | 10/1996 | Marik et al. |
| 5,601,563 A | 2/1997 | Burke et al. |
| 5,601,565 A | 2/1997 | Huebner |
| 5,662,656 A | 9/1997 | White |
| 5,681,354 A | 10/1997 | Eckhoff |
| 5,682,886 A | 11/1997 | Delp et al. |
| 5,683,398 A | 11/1997 | Carls et al. |
| 5,690,635 A | 11/1997 | Matsen, III et al. |
| 5,716,361 A | 2/1998 | Masini |
| 5,725,376 A | 3/1998 | Poirier |
| 5,735,277 A | 4/1998 | Schuster |
| 5,741,215 A | 4/1998 | D'Urso |
| 5,749,876 A | 5/1998 | Duvillier et al. |
| 5,755,803 A | 5/1998 | Haines et al. |
| 5,768,134 A | 6/1998 | Swaelens |
| 5,769,092 A | 6/1998 | Williamson, Jr. |
| 5,769,859 A | 6/1998 | Dorsey |
| D398,058 S | 9/1998 | Collier |
| 5,810,830 A | 9/1998 | Noble et al. |
| 5,824,085 A | 10/1998 | Sahay et al. |
| 5,824,098 A | 10/1998 | Stein |
| 5,824,100 A | 10/1998 | Kester et al. |
| 5,824,111 A | 10/1998 | Schell et al. |
| 5,860,980 A | 1/1999 | Axelson, Jr. et al. |
| 5,860,981 A | 1/1999 | Bertin et al. |
| 5,871,018 A * | 2/1999 | Delp et al. .................... 128/898 |
| 5,880,976 A | 3/1999 | DiGioia III et al. |
| 5,908,424 A | 6/1999 | Bertin et al. |
| 5,911,724 A | 6/1999 | Wehrli |
| 5,916,221 A | 6/1999 | Hodorek et al. |
| 5,964,808 A | 10/1999 | Blaha et al. |
| 5,967,777 A | 10/1999 | Klein et al. |
| 5,993,448 A | 11/1999 | Remmler |
| 5,995,738 A | 11/1999 | DiGioia, III et al. |
| 6,002,859 A | 12/1999 | DiGioia, III et al. |
| 6,068,658 A | 5/2000 | Insall et al. |
| 6,090,114 A | 7/2000 | Matsuno et al. |
| 6,096,043 A | 8/2000 | Techiera et al. |
| 6,106,529 A | 8/2000 | Techiera |
| 6,112,109 A | 8/2000 | D'Urso |
| 6,126,690 A | 10/2000 | Ateshian et al. |
| 6,132,447 A | 10/2000 | Dorsey |
| 6,161,080 A | 12/2000 | Aouni-Ateshian et al. |
| 6,171,340 B1 | 1/2001 | McDowell |
| 6,173,200 B1 | 1/2001 | Cooke et al. |
| 6,183,515 B1 | 2/2001 | Barlow et al. |
| 6,205,411 B1 | 3/2001 | DiGioia, III et al. |
| 6,228,121 B1 | 5/2001 | Khalili |
| 6,254,639 B1 | 7/2001 | Peckitt |
| 6,285,902 B1 | 9/2001 | Kienzle, III et al. |
| 6,327,491 B1 | 12/2001 | Franklin et al. |
| 6,343,987 B2 | 2/2002 | Hayama et al. |
| 6,382,975 B1 | 5/2002 | Poirier |
| 6,383,228 B1 | 5/2002 | Schmotzer |
| 6,385,475 B1 | 5/2002 | Cinquin et al. |
| 6,415,171 B1 | 7/2002 | Gueziec et al. |
| 6,458,135 B1 | 10/2002 | Harwin et al. |
| 6,463,351 B1 | 10/2002 | Clynch |
| 6,503,254 B2 | 1/2003 | Masini |
| 6,510,334 B1 | 1/2003 | Schuster et al. |
| 6,514,259 B2 | 2/2003 | Picard et al. |
| 6,520,964 B2 | 2/2003 | Tallarida et al. |
| 6,533,737 B1 | 3/2003 | Brosseau et al. |
| D473,307 S | 4/2003 | Cooke |
| 6,540,784 B2 | 4/2003 | Barlow et al. |
| 6,558,426 B1 | 5/2003 | Masini |
| 6,575,980 B1 | 6/2003 | Robie et al. |

(56) References Cited

U.S. PATENT DOCUMENTS

| | | |
|---|---|---|
| 6,602,259 B1 | 8/2003 | Masini |
| 6,672,870 B2 | 1/2004 | Knapp |
| 6,692,448 B2 | 2/2004 | Tanaka et al. |
| 6,701,174 B1 | 3/2004 | Krause et al. |
| 6,702,821 B2 | 3/2004 | Bonutti |
| 6,711,431 B2 | 3/2004 | Sarin et al. |
| 6,711,432 B1 | 3/2004 | Krause et al. |
| 6,712,856 B1 | 3/2004 | Carignan et al. |
| 6,716,249 B2 | 4/2004 | Hyde |
| 6,738,657 B1 | 5/2004 | Franklin et al. |
| 6,747,646 B2 | 6/2004 | Gueziec et al. |
| 6,770,099 B2 | 8/2004 | Andriacchi et al. |
| 6,772,026 B2 | 8/2004 | Bradbury et al. |
| 6,799,066 B2 | 9/2004 | Steines et al. |
| 6,814,575 B2 | 11/2004 | Poirier |
| 6,905,510 B2 | 6/2005 | Saab |
| 6,905,514 B2 | 6/2005 | Carignan et al. |
| 6,923,817 B2 | 8/2005 | Carson et al. |
| 6,932,842 B1 | 8/2005 | Litschko et al. |
| 6,944,518 B2 | 9/2005 | Roose |
| 6,969,393 B2 | 11/2005 | Pinczewski et al. |
| 6,975,894 B2 | 12/2005 | Wehrli et al. |
| 6,978,188 B1 | 12/2005 | Christensen |
| 7,029,479 B2 | 4/2006 | Tallarida et al. |
| 7,033,360 B2 | 4/2006 | Cinquin et al. |
| 7,039,225 B2 | 5/2006 | Tanaka et al. |
| 7,060,074 B2 | 6/2006 | Rosa et al. |
| 7,074,241 B2 | 7/2006 | McKinnon |
| 7,090,677 B2 | 8/2006 | Fallin et al. |
| 7,094,241 B2 | 8/2006 | Hodorek et al. |
| RE39,301 E | 9/2006 | Bertin |
| 7,104,997 B2 | 9/2006 | Lionberger et al. |
| 7,128,745 B2 | 10/2006 | Masini et al. |
| D532,515 S | 11/2006 | Buttler et al. |
| 7,141,053 B2 | 11/2006 | Rose et al. |
| 7,153,309 B2 | 12/2006 | Huebner et al. |
| 7,166,833 B2 | 1/2007 | Smith |
| 7,172,597 B2 | 2/2007 | Sanford |
| 7,174,282 B2 | 2/2007 | Hollister et al. |
| 7,184,814 B2 | 2/2007 | Lang et al. |
| 7,203,628 B1 | 4/2007 | St. Ville |
| 7,235,080 B2 | 6/2007 | Hodorek |
| 7,238,190 B2 | 7/2007 | Schon et al. |
| 7,239,908 B1 | 7/2007 | Alexander et al. |
| 7,258,701 B2 | 8/2007 | Aram et al. |
| 7,275,218 B2 | 9/2007 | Petrella et al. |
| 7,309,339 B2 | 12/2007 | Cusick et al. |
| 7,340,316 B2 | 3/2008 | Spaeth et al. |
| 7,359,746 B2 | 4/2008 | Arata |
| 7,373,286 B2 | 5/2008 | Nikolskiy et al. |
| 7,383,164 B2 | 6/2008 | Aram et al. |
| 7,388,972 B2 | 6/2008 | Kitson |
| 7,393,012 B2 | 7/2008 | Funakura et al. |
| 7,394,946 B2 | 7/2008 | Dewaele |
| 7,429,346 B2 | 9/2008 | Ensign et al. |
| 7,468,075 B2 | 12/2008 | Lang et al. |
| 7,547,307 B2 | 6/2009 | Carson et al. |
| 7,548,638 B2 * | 6/2009 | Graessner .................. 382/128 |
| 7,611,519 B2 | 11/2009 | Lefevre et al. |
| 7,616,800 B2 | 11/2009 | Paik et al. |
| 7,618,421 B2 | 11/2009 | Axelson, Jr. et al. |
| 7,618,451 B2 | 11/2009 | Berez et al. |
| 7,630,750 B2 | 12/2009 | Liang et al. |
| 7,634,119 B2 * | 12/2009 | Tsougarakis et al. ........ 382/128 |
| 7,634,306 B2 | 12/2009 | Sarin et al. |
| 7,641,660 B2 | 1/2010 | Lakin et al. |
| 7,643,862 B2 | 1/2010 | Schoenefeld |
| 7,693,321 B2 * | 4/2010 | Lehtonen-Krause ......... 382/131 |
| 7,702,380 B1 | 4/2010 | Dean |
| 7,715,602 B2 | 5/2010 | Richard |
| 7,717,956 B2 | 5/2010 | Lang |
| D618,796 S | 6/2010 | Cantu et al. |
| 7,747,305 B2 | 6/2010 | Dean et al. |
| D619,718 S | 7/2010 | Gannoe et al. |
| D622,854 S | 8/2010 | Otto et al. |
| 7,787,932 B2 | 8/2010 | Vilsmeier et al. |
| 7,794,467 B2 | 9/2010 | McGinley et al. |
| D626,234 S | 10/2010 | Otto et al. |
| 7,806,896 B1 | 10/2010 | Bonutti |
| 7,842,039 B2 | 11/2010 | Hodorek et al. |
| 7,842,092 B2 | 11/2010 | Otto et al. |
| 7,881,768 B2 | 2/2011 | Lang et al. |
| 7,927,335 B2 | 4/2011 | Deffenbaugh et al. |
| 7,950,924 B2 | 5/2011 | Brajnovic |
| 7,963,968 B2 | 6/2011 | Dees, Jr. |
| D642,263 S | 7/2011 | Park |
| 7,974,677 B2 | 7/2011 | Mire et al. |
| 8,007,448 B2 | 8/2011 | Moctezuma de la Barrera |
| 8,021,368 B2 | 9/2011 | Haines |
| 8,036,729 B2 | 10/2011 | Lang et al. |
| 8,052,623 B2 | 11/2011 | Haimerl et al. |
| 8,059,878 B2 | 11/2011 | Feilkas et al. |
| 8,077,950 B2 | 12/2011 | Tsougarakis et al. |
| 8,086,336 B2 | 12/2011 | Christensen |
| 8,115,485 B1 * | 2/2012 | Maier et al. .................. 324/318 |
| 8,126,533 B2 | 2/2012 | Lavallee |
| RE43,282 E | 3/2012 | Alexander et al. |
| 8,133,234 B2 | 3/2012 | Meridew et al. |
| 8,142,189 B2 | 3/2012 | Brajnovic |
| 8,160,345 B2 | 4/2012 | Pavlovskaia et al. |
| 8,170,716 B2 | 5/2012 | Coste-Maniere et al. |
| 8,177,850 B2 | 5/2012 | Rudan et al. |
| 8,202,324 B2 | 6/2012 | Meulink et al. |
| 8,214,016 B2 | 7/2012 | Lavallee et al. |
| 8,221,430 B2 | 7/2012 | Park et al. |
| 8,224,127 B2 | 7/2012 | Woodard et al. |
| 8,231,634 B2 | 7/2012 | Mahfouz et al. |
| 8,234,097 B2 | 7/2012 | Steines et al. |
| 8,241,293 B2 | 8/2012 | Stone et al. |
| 8,265,949 B2 | 9/2012 | Haddad |
| 8,306,601 B2 | 11/2012 | Lang et al. |
| 8,311,306 B2 | 11/2012 | Pavlovskaia et al. |
| 8,323,288 B2 | 12/2012 | Zajac |
| 8,331,634 B2 | 12/2012 | Barth et al. |
| 8,337,501 B2 | 12/2012 | Fitz et al. |
| 8,460,302 B2 | 6/2013 | Park et al. |
| 8,460,303 B2 | 6/2013 | Park |
| 8,480,679 B2 | 7/2013 | Park |
| 8,483,469 B2 | 7/2013 | Pavlovskaia et al. |
| D691,719 S | 10/2013 | Park |
| 8,545,509 B2 | 10/2013 | Park et al. |
| 8,617,171 B2 | 12/2013 | Park et al. |
| 8,734,455 B2 | 5/2014 | Park et al. |
| 8,737,700 B2 | 5/2014 | Park et al. |
| 9,265,509 B2 | 2/2016 | Park et al. |
| 2002/0055783 A1 | 5/2002 | Tallarida et al. |
| 2002/0087274 A1 | 7/2002 | Alexander et al. |
| 2002/0160337 A1 | 10/2002 | Klein et al. |
| 2003/0009167 A1 | 1/2003 | Wozencroft |
| 2003/0055502 A1 | 3/2003 | Lang et al. |
| 2003/0176783 A1 | 9/2003 | Hu |
| 2003/0216669 A1 | 11/2003 | Lang et al. |
| 2004/0097952 A1 | 5/2004 | Sarin et al. |
| 2004/0102792 A1 | 5/2004 | Sarin et al. |
| 2004/0102866 A1 | 5/2004 | Harris et al. |
| 2004/0133276 A1 | 7/2004 | Lang et al. |
| 2004/0138754 A1 | 7/2004 | Lang et al. |
| 2004/0146369 A1 | 7/2004 | Kato |
| 2004/0147927 A1 | 7/2004 | Tsougarakis et al. |
| 2004/0152970 A1 | 8/2004 | Hunter et al. |
| 2004/0153066 A1 | 8/2004 | Coon et al. |
| 2004/0153079 A1 | 8/2004 | Tsougarakis et al. |
| 2004/0153087 A1 | 8/2004 | Sanford et al. |
| 2004/0171924 A1 | 9/2004 | Mire et al. |
| 2004/0204760 A1 | 10/2004 | Fitz et al. |
| 2004/0220583 A1 | 11/2004 | Pieczynski, II et al. |
| 2004/0236424 A1 | 11/2004 | Berez et al. |
| 2004/0243148 A1 | 12/2004 | Wasielewski |
| 2004/0243481 A1 * | 12/2004 | Bradbury et al. ............. 705/26 |
| 2004/0254584 A1 | 12/2004 | Sarin et al. |
| 2005/0054914 A1 | 3/2005 | Duerk et al. |
| 2005/0059978 A1 | 3/2005 | Sherry et al. |
| 2005/0065617 A1 | 3/2005 | Moctezuma de la Barrera |
| 2005/0080426 A1 | 4/2005 | Qian |

(56) References Cited

U.S. PATENT DOCUMENTS

| | | |
|---|---|---|
| 2005/0096535 A1 | 5/2005 | Moctezuma de la Barrera |
| 2005/0113841 A1 | 5/2005 | Sheldon et al. |
| 2005/0119664 A1 | 6/2005 | Carignan et al. |
| 2005/0148843 A1 | 7/2005 | Roose |
| 2005/0148860 A1 | 7/2005 | Liew et al. |
| 2005/0149091 A1 | 7/2005 | Tanamal et al. |
| 2005/0192588 A1 | 9/2005 | Garcia |
| 2005/0197562 A1* | 9/2005 | Graessner ............ G01R 33/54 600/410 |
| 2005/0201509 A1* | 9/2005 | Mostafavi et al. ............ 378/8 |
| 2005/0216024 A1 | 9/2005 | Massoud |
| 2005/0234461 A1 | 10/2005 | Burdulis, Jr. et al. |
| 2005/0245934 A1 | 11/2005 | Tuke et al. |
| 2005/0245936 A1 | 11/2005 | Tuke et al. |
| 2005/0256389 A1 | 11/2005 | Koga et al. |
| 2005/0267584 A1 | 12/2005 | Burdulis, Jr. et al. |
| 2005/0272998 A1 | 12/2005 | Diehl et al. |
| 2006/0015018 A1 | 1/2006 | Jutras et al. |
| 2006/0015030 A1 | 1/2006 | Poulin et al. |
| 2006/0015188 A1 | 1/2006 | Grimes |
| 2006/0030853 A1 | 2/2006 | Haines |
| 2006/0036257 A1 | 2/2006 | Steffensmeier |
| 2006/0050945 A1* | 3/2006 | Lehtonen-Krause ........ 382/132 |
| 2006/0079755 A1* | 4/2006 | Stazzone et al. ............ 600/410 |
| 2006/0110017 A1 | 5/2006 | Tsai et al. |
| 2006/0111628 A1 | 5/2006 | Tsai et al. |
| 2006/0122491 A1 | 6/2006 | Murray et al. |
| 2006/0155293 A1 | 7/2006 | McGinley et al. |
| 2006/0155294 A1 | 7/2006 | Steffensmeier et al. |
| 2006/0161167 A1 | 7/2006 | Myers |
| 2006/0195113 A1 | 8/2006 | Masini |
| 2006/0244448 A1 | 11/2006 | Ballon et al. |
| 2006/0271058 A1 | 11/2006 | Ashton et al. |
| 2006/0293681 A1 | 12/2006 | Claypool et al. |
| 2007/0005073 A1 | 1/2007 | Claypool et al. |
| 2007/0010732 A1 | 1/2007 | DeYoe et al. |
| 2007/0021838 A1 | 1/2007 | Dugas et al. |
| 2007/0038059 A1 | 2/2007 | Sheffer et al. |
| 2007/0055268 A1 | 3/2007 | Utz et al. |
| 2007/0073305 A1 | 3/2007 | Lionberger et al. |
| 2007/0083266 A1 | 4/2007 | Lang |
| 2007/0100338 A1 | 5/2007 | Deffenbaugh et al. |
| 2007/0100462 A1 | 5/2007 | Lang et al. |
| 2007/0106389 A1 | 5/2007 | Croxton et al. |
| 2007/0114370 A1 | 5/2007 | Smith et al. |
| 2007/0118055 A1 | 5/2007 | McCombs |
| 2007/0118243 A1 | 5/2007 | Schroeder et al. |
| 2007/0123856 A1 | 5/2007 | Deffenbaugh et al. |
| 2007/0123857 A1 | 5/2007 | Deffenbaugh et al. |
| 2007/0123912 A1 | 5/2007 | Carson |
| 2007/0162039 A1 | 7/2007 | Wozencroft |
| 2007/0167833 A1* | 7/2007 | Redel et al. ............... 600/476 |
| 2007/0173853 A1 | 7/2007 | MacMillan |
| 2007/0173858 A1 | 7/2007 | Engh et al. |
| 2007/0191703 A1* | 8/2007 | Graf ........................ 600/410 |
| 2007/0191741 A1 | 8/2007 | Tsai et al. |
| 2007/0198022 A1 | 8/2007 | Lang et al. |
| 2007/0211928 A1 | 9/2007 | Weng et al. |
| 2007/0213738 A1 | 9/2007 | Martin et al. |
| 2007/0219560 A1 | 9/2007 | Hodorek |
| 2007/0226986 A1* | 10/2007 | Park et al. ................. 29/592 |
| 2007/0232959 A1 | 10/2007 | Couture et al. |
| 2007/0233136 A1 | 10/2007 | Wozencroft |
| 2007/0233140 A1 | 10/2007 | Metzger et al. |
| 2007/0233141 A1 | 10/2007 | Park et al. |
| 2007/0233269 A1 | 10/2007 | Steines et al. |
| 2007/0237372 A1* | 10/2007 | Chen et al. ............... 382/128 |
| 2007/0238973 A1* | 10/2007 | Krueger ................... 600/410 |
| 2007/0239167 A1 | 10/2007 | Pinczewski et al. |
| 2007/0249967 A1 | 10/2007 | Buly et al. |
| 2007/0276224 A1 | 11/2007 | Lang et al. |
| 2007/0276400 A1 | 11/2007 | Moore et al. |
| 2007/0282451 A1 | 12/2007 | Metzger et al. |
| 2007/0288030 A1 | 12/2007 | Metzger et al. |
| 2008/0004701 A1 | 1/2008 | Axelson et al. |
| 2008/0015433 A1 | 1/2008 | Alexander et al. |
| 2008/0015599 A1 | 1/2008 | D'Alessio et al. |
| 2008/0015600 A1 | 1/2008 | D'Alessio et al. |
| 2008/0015602 A1 | 1/2008 | Axelson et al. |
| 2008/0015606 A1 | 1/2008 | Axelson et al. |
| 2008/0015607 A1 | 1/2008 | Axelson et al. |
| 2008/0021299 A1 | 1/2008 | Meulink |
| 2008/0031412 A1 | 2/2008 | Lang et al. |
| 2008/0033442 A1 | 2/2008 | Amiot et al. |
| 2008/0058613 A1 | 3/2008 | Lang et al. |
| 2008/0088761 A1 | 4/2008 | Lin et al. |
| 2008/0089591 A1 | 4/2008 | Zhou et al. |
| 2008/0114370 A1 | 5/2008 | Schoenefeld |
| 2008/0137926 A1 | 6/2008 | Skinner et al. |
| 2008/0147072 A1 | 6/2008 | Park et al. |
| 2008/0153067 A1 | 6/2008 | Berckmans et al. |
| 2008/0161815 A1 | 7/2008 | Schoenefeld et al. |
| 2008/0195108 A1 | 8/2008 | Bhatnagar et al. |
| 2008/0208081 A1* | 8/2008 | Murphy ................ A61B 90/36 600/595 |
| 2008/0215059 A1 | 9/2008 | Carignan et al. |
| 2008/0232661 A1* | 9/2008 | Habets ................ G06T 7/0012 382/128 |
| 2008/0234685 A1 | 9/2008 | Gjerde |
| 2008/0243127 A1 | 10/2008 | Lang et al. |
| 2008/0257363 A1 | 10/2008 | Schoenefeld et al. |
| 2008/0262624 A1 | 10/2008 | White et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0286722 A1 | 11/2008 | Berckmans, III et al. |
| 2008/0287953 A1 | 11/2008 | Sers |
| 2008/0287954 A1 | 11/2008 | Kunz et al. |
| 2008/0312659 A1 | 12/2008 | Metzger et al. |
| 2008/0319491 A1 | 12/2008 | Schoenefeld |
| 2009/0024131 A1 | 1/2009 | Metzger et al. |
| 2009/0087276 A1 | 4/2009 | Rose |
| 2009/0088674 A1 | 4/2009 | Caillouette et al. |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aaram et al. |
| 2009/0088761 A1 | 4/2009 | Roose et al. |
| 2009/0088763 A1 | 4/2009 | Aram et al. |
| 2009/0089034 A1 | 4/2009 | Penney et al. |
| 2009/0093816 A1 | 4/2009 | Roose et al. |
| 2009/0110498 A1 | 4/2009 | Park |
| 2009/0112213 A1 | 4/2009 | Heavener et al. |
| 2009/0125114 A1 | 5/2009 | May et al. |
| 2009/0131941 A1 | 5/2009 | Park et al. |
| 2009/0131942 A1 | 5/2009 | Aker et al. |
| 2009/0151736 A1 | 6/2009 | Belcher et al. |
| 2009/0157083 A1 | 6/2009 | Park et al. |
| 2009/0163923 A1 | 6/2009 | Flett et al. |
| 2009/0222014 A1 | 9/2009 | Bojarski et al. |
| 2009/0222015 A1 | 9/2009 | Park et al. |
| 2009/0222016 A1 | 9/2009 | Park et al. |
| 2009/0222103 A1 | 9/2009 | Fitz et al. |
| 2009/0248044 A1 | 10/2009 | Amiot et al. |
| 2009/0254093 A1 | 10/2009 | White et al. |
| 2009/0254367 A1 | 10/2009 | Belcher et al. |
| 2009/0270868 A1 | 10/2009 | Park et al. |
| 2009/0274350 A1 | 11/2009 | Pavlovskaia et al. |
| 2009/0276045 A1 | 11/2009 | Lang |
| 2009/0306676 A1 | 12/2009 | Lang et al. |
| 2009/0307893 A1 | 12/2009 | Burdulis, Jr. et al. |
| 2009/0312805 A1 | 12/2009 | Lang et al. |
| 2010/0023015 A1 | 1/2010 | Park |
| 2010/0042105 A1 | 2/2010 | Park et al. |
| 2010/0049195 A1 | 2/2010 | Park et al. |
| 2010/0087829 A1 | 4/2010 | Metzger et al. |
| 2010/0145344 A1 | 6/2010 | Jordan et al. |
| 2010/0152741 A1 | 6/2010 | Park et al. |
| 2010/0160917 A1 | 6/2010 | Fitz et al. |
| 2010/0168754 A1 | 7/2010 | Fitz et al. |
| 2010/0174376 A1 | 7/2010 | Lang |

(56) References Cited

U.S. PATENT DOCUMENTS

| | | |
|---|---|---|
| 2010/0191242 A1 | 7/2010 | Massoud |
| 2010/0198351 A1 | 8/2010 | Meulink |
| 2010/0209868 A1 | 8/2010 | De Clerck |
| 2010/0228257 A1 | 9/2010 | Bonutti |
| 2010/0256479 A1 | 10/2010 | Park et al. |
| 2010/0274534 A1 | 10/2010 | Steines et al. |
| 2010/0298894 A1 | 11/2010 | Bojarski et al. |
| 2010/0303313 A1 | 12/2010 | Lang et al. |
| 2010/0303317 A1 | 12/2010 | Tsougarakis et al. |
| 2010/0303324 A1 | 12/2010 | Lang et al. |
| 2010/0305574 A1 | 12/2010 | Fitz et al. |
| 2010/0305708 A1 | 12/2010 | Lang et al. |
| 2010/0305907 A1 | 12/2010 | Fitz et al. |
| 2010/0324692 A1 | 12/2010 | Uthgenannt et al. |
| 2010/0329530 A1 | 12/2010 | Lang et al. |
| 2011/0015636 A1 | 1/2011 | Katrana et al. |
| 2011/0029093 A1 | 2/2011 | Bojarski et al. |
| 2011/0029116 A1 | 2/2011 | Jordan et al. |
| 2011/0046735 A1 | 2/2011 | Metzger et al. |
| 2011/0066193 A1 | 3/2011 | Lang et al. |
| 2011/0066245 A1 | 3/2011 | Lang et al. |
| 2011/0071533 A1 | 3/2011 | Metzger et al. |
| 2011/0071537 A1 | 3/2011 | Koga et al. |
| 2011/0071581 A1 | 3/2011 | Lang et al. |
| 2011/0087332 A1 | 4/2011 | Bojarski et al. |
| 2011/0087465 A1 | 4/2011 | Mahfouz |
| 2011/0092804 A1 | 4/2011 | Schoenefeld et al. |
| 2011/0092978 A1 | 4/2011 | McCombs |
| 2011/0144760 A1 | 6/2011 | Wong et al. |
| 2011/0160736 A1 | 6/2011 | Meridew et al. |
| 2011/0166578 A1 | 7/2011 | Stone et al. |
| 2011/0166666 A1 | 7/2011 | Meulink et al. |
| 2011/0172672 A1 | 7/2011 | Dubeau et al. |
| 2011/0184526 A1 | 7/2011 | White et al. |
| 2011/0190775 A1 | 8/2011 | Ure |
| 2011/0190899 A1 | 8/2011 | Pierce et al. |
| 2011/0213368 A1 | 9/2011 | Fitz et al. |
| 2011/0213373 A1 | 9/2011 | Fitz et al. |
| 2011/0213374 A1 | 9/2011 | Fitz et al. |
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0214279 A1 | 9/2011 | Park |
| 2011/0218539 A1 | 9/2011 | Fitz et al. |
| 2011/0218584 A1 | 9/2011 | Fitz et al. |
| 2011/0230888 A1 | 9/2011 | Lang et al. |
| 2011/0238073 A1 | 9/2011 | Lang et al. |
| 2011/0266265 A1 | 11/2011 | Lang |
| 2011/0268248 A1 | 11/2011 | Simon et al. |
| 2011/0270072 A9 | 11/2011 | Feilkas et al. |
| 2011/0276145 A1 | 11/2011 | Carignan et al. |
| 2011/0282473 A1 | 11/2011 | Pavlovskaia et al. |
| 2011/0295329 A1 | 12/2011 | Fitz et al. |
| 2011/0295378 A1 | 12/2011 | Bojarski et al. |
| 2011/0313423 A1 | 12/2011 | Lang et al. |
| 2011/0319897 A1 | 12/2011 | Lang et al. |
| 2011/0319900 A1 | 12/2011 | Lang et al. |
| 2012/0029520 A1 | 2/2012 | Lang et al. |
| 2012/0041446 A1 | 2/2012 | Wong et al. |
| 2012/0053591 A1 | 3/2012 | Haines et al. |
| 2012/0065640 A1 | 3/2012 | Metzger et al. |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0093377 A1 | 4/2012 | Tsougarakis et al. |
| 2012/0101503 A1 | 4/2012 | Lang et al. |
| 2012/0143197 A1 | 6/2012 | Lang et al. |
| 2012/0150243 A9 | 6/2012 | Crawford et al. |
| 2012/0151730 A1 | 6/2012 | Fitz et al. |
| 2012/0158001 A1 | 6/2012 | Burdulis, Jr. et al. |
| 2012/0158002 A1 | 6/2012 | Carignan et al. |
| 2012/0165821 A1 | 6/2012 | Carignan et al. |
| 2012/0191205 A1 | 7/2012 | Bojarski et al. |
| 2012/0191420 A1 | 7/2012 | Bojarski et al. |
| 2012/0192401 A1 | 8/2012 | Pavlovskaia et al. |
| 2012/0197260 A1 | 8/2012 | Fitz et al. |
| 2012/0197408 A1 | 8/2012 | Lang et al. |
| 2012/0215226 A1 | 8/2012 | Bonutti |
| 2012/0230566 A1 | 9/2012 | Dean et al. |
| 2012/0232669 A1 | 9/2012 | Bojarski et al. |
| 2012/0232670 A1 | 9/2012 | Bojarski et al. |
| 2012/0232671 A1 | 9/2012 | Bojarski et al. |
| 2012/0265499 A1 | 10/2012 | Mahfouz et al. |
| 2012/0310400 A1 | 12/2012 | Park |
| 2013/0115474 A1 | 5/2013 | Park |
| 2013/0116697 A1 | 5/2013 | Park et al. |
| 2013/0123789 A1 | 5/2013 | Park |
| 2013/0190767 A1 | 7/2013 | Park et al. |
| 2013/0345845 A1 | 12/2013 | Park et al. |
| 2014/0078139 A1 | 3/2014 | Park et al. |
| 2014/0330278 A1 | 11/2014 | Park et al. |
| 2014/0330279 A1 | 11/2014 | Park et al. |
| 2014/0378978 A1 | 12/2014 | Park |
| 2016/0015466 A1 | 1/2016 | Park et al. |
| 2016/0095609 A1 | 4/2016 | Park et al. |
| 2016/0228194 A1 | 8/2016 | Park et al. |
| 2016/0228195 A1 | 8/2016 | Park et al. |
| 2016/0228196 A1 | 8/2016 | Park et al. |
| 2016/0228197 A1 | 8/2016 | Park et al. |

FOREIGN PATENT DOCUMENTS

| | | |
|---|---|---|
| DE | 10 2005 023 028 A1 | 11/2006 |
| EP | 0097001 A | 12/1983 |
| EP | 0574098 A | 12/1993 |
| EP | 0622052 A | 11/1994 |
| EP | 0709061 A1 | 5/1996 |
| EP | 0908836 A2 | 4/1999 |
| EP | 0908836 A3 | 12/1999 |
| EP | 1059153 A2 | 12/2000 |
| EP | 1486900 | 12/2004 |
| EP | 1 532 939 A1 | 5/2005 |
| EP | 1669033 A1 | 6/2006 |
| FR | 2478462 A1 | 9/1981 |
| GB | 2215610 | 9/1989 |
| GB | 2420717 A | 6/2006 |
| GB | 2447702 A | 9/2008 |
| JP | 10-94538 | 4/1998 |
| JP | 2001-092950 | 4/2001 |
| JP | 2005-287813 | 10/2005 |
| WO | WO 93/025157 | 12/1993 |
| WO | WO 95/007509 A1 | 3/1995 |
| WO | WO 95/27450 | 10/1995 |
| WO | WO 97/023172 A2 | 7/1997 |
| WO | WO 98/012995 A2 | 4/1998 |
| WO | WO 98/32384 | 7/1998 |
| WO | WO 00/35346 | 6/2000 |
| WO | WO 01/000096 | 1/2001 |
| WO | WO 01/070142 | 9/2001 |
| WO | WO 01/85040 A1 | 11/2001 |
| WO | WO 02/096268 A2 | 12/2002 |
| WO | WO 04/032806 | 4/2004 |
| WO | WO 04/049981 | 6/2004 |
| WO | WO 05/051240 | 6/2005 |
| WO | WO 2005/087125 A2 | 9/2005 |
| WO | WO 06/058057 | 6/2006 |
| WO | WO 06/060795 | 6/2006 |
| WO | WO 06/092600 | 9/2006 |
| WO | WO 2006/127486 A2 | 11/2006 |
| WO | WO 2006/134345 A1 | 12/2006 |
| WO | WO 07/014164 | 2/2007 |
| WO | WO 2007/058632 A1 | 5/2007 |
| WO | WO 2007/092841 A2 | 8/2007 |
| WO | WO 2007/097853 A2 | 8/2007 |
| WO | WO 2007/097854 A2 | 8/2007 |
| WO | WO 2007/137327 A1 | 12/2007 |

(56) References Cited

FOREIGN PATENT DOCUMENTS

WO    WO 2008/014618 A1    2/2008
WO    WO 2008/091358 A1    7/2008

OTHER PUBLICATIONS

Calvo et al., "High-resolution MRI detects cartilage swellilng at the earlyl stages of experimental osteorthritis", OARSI, 2001, pp. 463-472.*
Akenine-Möller et al., *Real-Time Rendering, Second Edition*, AK Peters, Natick, MA, 6 pages (Table of Contents), 2002.
Author Unknown, "MRI Protocol Reference," ConforMIS, Inc., copyright 2007, http://www.conformis.com/Imaging-Professionals/MRI-Protocol-Guides, last visited on Mar. 28, 2008, 18 pages.
Author Unknown, "MRI Protocol Reference Guide for GE Systems," ConforMIS, Inc., copyright 2007, http://www.conformis.com/Imaging-Professionals/MRI-Protocol-Guides, last visited on Mar. 28, 2008, 18 pages.
Author Unknown, "MRI Protocol Reference Guide for Phillips Systems," ConforMIS, Inc., copyright 2007, http://www.conformis.com/Imaging-Professionals/MRI-Protocol-Guides, last visited on Mar. 28, 2008, 19 pages.
Author Unknown, "MRI Protocol Reference Guide for Siemens Systems," ConforMIS, Inc., copyright 2007, http://www.conformis.com/Imaging-Professionals/MRI-Protocol-Guides, last visited on Mar. 28, 2008, 18 pages.
Barequet et al., "Filling Gaps in the Boundary of a Polyhedron," *Computer Aided Geometric Design*, vol. 12, pp. 207-229, 1995.
Barequet et al., "Repairing CAD Models," Proceedings of the 8th IEEE Visualization '97 Conference, pp. 363-370, Oct. 1997.
Berry et al., "Personalised image-based templates for intra-operative guidance," *Proc. Inst. Mech. Eng. Part H: J. Engineering in Medicine*, vol. 219, pp. 111-118, Oct. 7, 2004.
Bibčević et al., "Variations of Femoral Condyle Shape," *Coll. Antropol.*, vol. 29 No. 2, pp. 409-414, 2005.
Blinn, *Jim Blinn's Corner—A Trip Down the Graphics Pipeline*, Morgan Kaufmann Publishers, Inc., San Francisco, CA, 5 pages (Table of Contents), 1996.
Bøhn et al., "A Topology-Based Approach for Shell-Closure," *Geometric Modeling for Product Realization* (P.R. Wilson et al. editors), pp. 297-319, Elsevier Science Publishers B.V., North-Holland, 1993.
Chauhan et al., "Computer-assisted knee arthroplasty versus a conventional jig-based technique—a randomised, prospective trial," *The Journal of Bone and Joint Surgery*, vol. 86-B, No. 3, pp. 372-377, Apr. 2004.
Cohen et al., *Radiosity and Realistic Image Synthesis*, Academic Press Professional, Cambridge, MA, 8 pages (Table of Contents), 1993.
Couglin et al., "Tibial Axis and Patellar Position Relative to the Femoral Epicondylar Axis During Squatting," *The Journal of Arthroplasty*, vol. 18, No. 8, Elsevier, 2003.
Delp et al., "Computer Assisted Knee Replacement," *Clinical Orthopaedics and Related Research*, No. 354, pp. 49-56, Sep. 1998.
Dutré et al., *Advanced Global Illumination*, AK Peters, Natick, MA, 5 pages (Table of Contents), 2003.
Eckhoff et al., "Three-Dimensional Mechanics, Kinematics, and Morphology of the Knee Viewed in Virtual Realty," *The Journal of Bone and Joint Surgery*, vol. 87-A, Supplement 2, pp. 71-80, 2005.
Erikson, "Error Correction of a Large Architectural Model: The Henderson County Courthouse," Technical Report TR95-013, Dept. of Computer Science, University of North Carolina at Chapel Hill, pp. 1-11, 1995.
Ervin et al., *Landscape Modeling*, McGraw-Hill, New York, NY, 8 pages (Table of Contents), 2001.
Farin, *NURB Curves and Surfaces: From Projective Geometry to Practical Use*, AK Peters, Wellesley, MA, 7 pages (Table of Contents), 1995.

Fleischer et al., "Accurate Polygon Scan Conversion Using Half-Open Intervals," *Graphics Gems III*, pp. 362-365, code: pp. 599-605, 1992.
Foley et al., *Computer Graphics: Principles and Practice*, Addison-Wesley Publishing Company, Reading, MA, 9 pages (Table of Contents), 1990.
Glassner (editor), *An Introduction to Ray Tracing*, Academic Press Limited, San Diego, CA, 4 pages (Table of Contents), 1989.
Glassner, *Principles of Digital Image Synthesis*, Volumes One and Two, Morgan Kaufmann Publishers, Inc., San Francisco, CA, 32 pages (Table of Contents), 1995.
Gooch et al., *Non-Photorealistic Rendering*, AK Peters, Natick, MA, 4 pages (Table of Contents), 2001.
Grüne et al., "On numerical algorithm and interactive visualization for optimal control problems," *Journal of Computation and Visualization in Science*, vol. 1, No. 4, pp. 221-229, Jul. 1999.
Guéziec et al., "Converting Sets of Polygons to Manifold Surfaces by Cutting and Stitching," Proc. IEEE Visualization 1998, pp. 383-390, Oct. 1998.
Hafez et al., "Patient Specific Instrumentation for TKA: Testing the Reliability Using a Navigational System," MIS Meets CAOS Symposium & Instructional Academy, Less and Minimally Invasive Surgery for Joint Arthroplasty: FACT and FICTION Syllabus, San Diego, CA, 8 pages, Oct. 20-22, 2005 (best available copy).
Hafez et al., "Computer Assisted Total Knee Replacement: Could a Two-Piece Custom Template Replace the Complex Conventional Instrumentations?", *Computer Aided Surgery*, vol. 9, No. 3, pp. 93-94, 2004.
Hafez et al., "Computer-Assisted Total Knee Arthroplasty Using Patient-Specific Templating," *Clinical Orthopaedics and Related Research*, No. 0, pp. 1-9, 2006.
Jensen, *Realistic Image Synthesis Using Photon Mapping*, AK Peters, Natick, MA, 7 pages (Table of Contents), 2001.
Jones et al., "A new approach to the construction of surfaces from contour data," *Computer Graphics Forum*, vol. 13, No. 3, pp. 75-84, 1994 [ISSN 0167-7055].
Khorramabadi, "A Walk Through the Planned CS Building," Technical Report UCB/CSD 91/652, Computer Science Department, University of California at Berkeley, 74 pages, 1991.
Kidder et al., "3-D Model Acquisition, Design, Planning and Manufacturing of Orthopaedic Devices: A Framework," *Advanced Sensor and Control-System Interface* (B.O. Nnaji editor), Proceedings SPIE—The International Society for Optical Engineering, Bellingham, WA, vol. 2911, pp. 9-22, Nov. 21-22, 1996.
Kumar, *Robust Incremental Polygon Triangulation for Surface Rendering*, Center for Geometric Computing, Department of Computer Science, Johns Hopkins University, Baltimore, MD, WSCG, The International Conference in Central Europe on Computer Graphics, Visualization and Computer Vision, pp. 381-388, 2000.
Lorensen et al., "Marching Cubes: A High Resolution 3d Surface Construction Algorithm," *Computer Graphics*, vol. 21, No. 4, pp. 163-169, 1987.
Morvan et al., IVECS, Interactively Correcting .STL Files in a Virtual Environment, Clemson University, Clemson, SC, Proc. Conf. Virtual Design, Aug. 1996.
Nooruddin et al., Simplification and Repair of Polygonal Models Using Volumetric Techniques, *IEEE Transactions on Visualization and Computer Graphics*, vol. 9, No. 2, pp. 191-205, Apr.-Jun. 2003.
Pharr et al., *Physically Based Rendering, from Theory to Implementation*, Morgan Kaufmann Publishers, San Francisco, CA, 13 pages (Table of Contents), 2004.
Platt et al., "Mould Arthroplasty of the Knee, A Ten-Year Follow-up Study," *The Journal of Bone and Joint Surgery* (British Volume), vol. 51-B, No. 1, pp. 76-87, Feb. 1969.
Potter, "Arthroplasty of the Knee with Tibial Metallic Implants of the McKeever and Macintosh Design," *The Surgical Clinics of North America*, vol. 49, No. 4, pp. 903-915, Aug. 1969.
Radermacher et al., "Computer Assisted Orthopaedic Surgery with Image Based Individual Templates," *Clinical Orthopaedics and Related Research*, vol. 354, pp. 28-38, Sep. 1998.
Rohlfing et al., "*Quo Vadis*, Atlas-Based Segmentation?", *The Handbook of Medical Image Analysis: Segmentation and Registra-*

(56) References Cited

OTHER PUBLICATIONS

*tion Models* (Kluwer), pp. 1-55, (http://www.stanford.edu/~rohlfing/publications/2005-rohlfing-chapter-quo_vadis_atlas_based_segmentation.pdf).

Shirley et al., *Realistic Ray Tracing, Second Edition*, AK Peters, Natick, MA, 7 pages (Table of Contents), 2003.

Strothotte et al., *Non-Photorealistic Computer Graphics—Modeling, Rendering, and Animation*, Morgan Kaufmann Publishers, San Francisco, CA, 9 pages (Table of Contents), 2002.

Vande Berg et al., "Assessment of Knee Cartilage in Cadavers with Dual-Detector Spiral CT Arthrography and MR Imaging," *Radiology*, vol. 222, No. 2, pp. 430-436, Feb. 2002.

Wikipedia, the Free Encyclopedia, "CNC," (date unknown) located at http://en.wikipedia.org/wiki/CNC>, 6 pages, last visited on Apr. 12, 2007.

Office Action, U.S. Appl. No. 10/146,862, dated Jan. 13, 2005, 10 pages.

Amendment and Response to Office Action and Petition to Revive, U.S. Appl. No. 10/146,862, filed Jan. 18, 2006, 29 pages.

International Search Report and Written Opinion, PCT/US2007/001624, dated Dec. 12, 2007, 14 pages.

Invitation to Pay Additional Fees mailed on Jul. 31, 2007, for PCT Application No. PCT/US2007/001624 filed on Jan. 19, 2007, 5 pages.

International Search Report and Written Opinion, PCT/US2007/001622, dated Jun. 11, 2007, 14 pages.

Amendment and Response to Non-Final Office Action, U.S. Appl. No. 11/959,344, dated Jul. 15, 2011, 13 pages.

International Search Report and Written Opinion, PCT/US2011/032342, dated Jul. 1, 2011, 8 pages.

Non-Final Office Action, U.S. Appl. No. 11/641,569, dated Aug. 3, 2011, 14 pages.

Non-Final Office Action, U.S. Appl. No. 12/390,667, dated Aug. 24, 2011, 49 pages.

Response to Restriction Requirement, U.S. Appl. No. 12/390,667, dated Jul. 27, 2011, 8 pages.

Response to Restriction Requirement, U.S. Appl. No. 12/391,008, filed Aug. 29, 2011, 9 pages.

Restriction Requirement, U.S. Appl. No. 12/390,667, dated Jul. 14, 2011, 9 pages.

Restriction Requirement, U.S. Appl. No. 12/391,008, dated Aug. 18, 2011, 6 pages.

U.S. Appl. No. 29/394,882, filed Jun. 22, 2011, Ilwhan Park.

International Search Report and Written Opinion, International Application No. PCT/US2009/040629, dated Aug. 6, 2009, 9 pages.

Restriction Requirement, U.S. Appl. No. 11/641,382, dated Sep. 3, 2009, 6 pages.

Restriction Requirement, U.S. Appl. No. 11/642,385, dated Oct. 27, 2009, 7 pages.

International Search Report and Written Opinion, International Application No. PCT/US2009/051109, dated Nov. 6, 2009, 13 pages.

NonFinal Office Action, U.S. Appl. No. 11/641,569, dated Nov. 12, 2009, 9 pages.

Restriction Requirement, U.S. Appl. No. 11/656,323, dated Nov. 13, 2009, 10 pages.

Restriction Requirement, U.S. Appl. No. 11/641,569, dated Apr. 27, 2009, 7 pages.

International Search Report and Written Opinion, International Application No. PCT/US2009/34983, dated May 22, 2009, 15 pages.

International Search Report and Written Opinion, International Application No. PCT/US2009/034967, dated Jun. 16, 2009, 15 pages.

International Search Report and Written Opinion, International Application No. PCT/US2009/041519, dated Jun. 17, 2009, 10 pages.

Kunz et al., "Computer Assisted Hip Resurfacing Using Individualized Drill Templates," The Journal of Arthroplasty, vol. 00, No. 0, pp. 1-7, 2009.

Advisory Action, U.S. Appl. No. 11/642,385, dated Oct. 29, 2010, 3 pages.

Amendment and Response to Ex Parte Quayle Action, U.S. Appl. No. 29/296,687 dated Mar. 24, 2011, 17 pages.

Amendment and Response to Final Office Action, U.S. Appl. No. 11/642,385, filed Oct. 4, 2010, 16 pages.

Amendment and Response to Non-Final Office Action, U.S. Appl. No. 11/641,382, dated Apr. 20, 2010, 23 pages.

Amendment and Response to Office Action, U.S. Appl. No. 11/656,323, filed Jun. 25, 2010, 7 pages.

Amendment and Response to Office Action, U.S. Appl. No. 11/641,569, dated Feb. 5, 2010, 20 pages.

Amendment and Response to Restriction Requirement, U.S. Appl. No. 11/641,569, dated May 27, 2009, 12 pages.

Amendment and Response to Restriction Requirement, U.S. Appl. No. 11/641,382, dated Oct. 5, 2009, 10 pages.

Amendment and Response to Restriction Requirement, U.S. Appl. No. 11/642,385, filed Nov. 24, 2009, 10 pages.

Amendment and Response to Restriction/Election Requirement, U.S. Appl. No. 11/656,323, filed Dec. 8, 2009, 6 pages.

Amendment and Response, U.S. Appl. No. 11/642,385, filed May 28, 2010, 11 pages.

European Search Report, 10192631.9-2310, dated Mar. 17, 2011, 5 pages.

Ex Parte Quayle Action, U.S. Appl. No. 29/296,687, dated Jan. 24, 2011, 11 pages.

Final Office Action and PTO-892, U.S. Appl. No. 11/641,382 dated Aug. 5, 2010, 13 pages.

Final Office Action and PTO-892. U.S. Appl. No. 11/656,323, dated Sep. 3, 2010, 11 pages.

Final Office Action, U.S. Appl. No. 11/641,569, dated May 10, 2010, 9 pages.

International Search Report and Written Opinion, International Application No. PCT/US2009/058946, dated Jan. 28, 2010, 14 pages.

International Search Report and Written Opinion, International Application No. PCT/US2009/068055, dated Mar. 11, 2010, 10 pages.

Non-Final Office Action and PTO-892, U.S. Appl. No. 11/641,382, dated Jan. 20, 2010. 12 pages.

Non Final Office Action and PTO-892, U.S. Appl. No. 11/642,385, dated Mar. 2, 2010, 11 pages.

Non-Final Office Action and PTO-892, U.S. Appl. No. 11/656,323, dated Mar. 30, 2010, 10 pages.

Nonfinal Office Action, U.S. Appl. No. 11/959,344, dated Feb. 15, 2011, 29 pages.

Notice of Allowance, U.S. Appl. No. 29,296,687, dated Mar. 31, 2011, 18 pages.

Notice of Non-Compliant Amendment, U.S. Appl. No. 11/641,569, dated Aug. 7, 2009, 3 pages.

Preliminary Amendment, U.S. Appl. No. 11/641,569, dated Aug. 14, 2008, 13 pages.

Preliminary Amendment, U.S. Appl. No. 11/642,385, filed Aug. 22, 2008, 42 pages.

RCE/Amendment, U.S. Appl. No. 11/641,569, filed Aug. 9, 2010, 18 pages.

RCE/Amendment, U.S. Appl. No. 11/642,382, filed Oct. 26, 2010, 14 pages.

RCE/Amendment, U.S. Appl. No. 11/642,385, filed Dec. 6, 2010, 13 pages.

RCE/Amendment, U.S. Appl. No. 11/656,323, filed Nov. 19, 2010, 12 pages.

Response to Notice of Non-Complaint Amendment, U.S. Appl. No. 11/641,669, dated Aug. 19, 2009, 11 pages.

Response to Restriction Requirement U.S. Appl. No. 29/296,687, filed Oct. 7, 2010, 3 pages.

Response to Restriction Requirement, U.S. Appl. No. 11/959,344, filed Nov. 24, 2010, 13 pages.

Restriction Requirement, U.S. Appl. No. 11/959,344, dated Oct. 29, 2010, 6 pages.

Restriction Requirement, U.S. Appl. No. 29/296,687, dated Sep. 21, 2010, 7 pages.

(56) References Cited

OTHER PUBLICATIONS

Akca, "Matching of 3D Surfaces and Their Intensities," ISPRS Journal of Photogrammetry & Remote Sensing, 62(2007), 112-121.
Arima et al., "Femoral Rotational Alignment, Based on the Anteroposterior Axis, in Total Knee Arthroplasty in a Valgus Knee. A Technical Note," Journal Bone Joint Surg Am. 1995;77(9):1331-4.
Bargar et al., "Robotic Systems in Surgery," Orthopedic and Spine Surgery, Surgical Technology International II, 1993, 419-423.
Besl et al., "A Method for Registration of 3-D Shapes," IEEE Transactions on Pattern Analysis and Machine Intelligence (PAMI), 14(2):239-256, Feb. 1992.
Blaha et al., "Using the Transepicondylar Axis to Define the Sagittal Morphology of the Distal Part of the Femur," J Bone Joint Surg Am. 2002;84-A Suppl 2:48-55.
Bullough et al., "The Geometry of Diarthrodial Joints, Its Physiologic Maintenance and the Possible significance of Age-Related Changes in Geometry-to-Load distribution and the Development of Osteoarthritis," Clin Orthop Rel Res 1981, 156:61-6.
Burgkart et al., "Magnetic Resonance Imaging-Based Assessment of Cartilage Loss in Severe Osteoarthritis: Accuracy, Precision, and Diagnostic Value," Arthritis Rheum 2001, 44:2072-7.
Canny, "A computational Approach to Edge Detection," IEEE Transactions on Pattern Analysis and Machine Intelligence, PAMI 8(6), pp. 679-698 (1986).
Churchill et al., "The Transepicondylar Axis Approximates the Optimal Flexion Axis of the Knee," Clin Orthop Relat Res. 1998(356):111-8.
Cicuttini et al., "Gender Differences in Knee Cartilage Volume as Measured by Magnetic Resonance Imaging," Osteoarthritis Cartilage 1999, 7:265-71.
Cicuttini et al., "Longitudinal Study of the Relationship Between Knee angle and Tibiofemoral cartilage Volume in Subjects with Knee Osteoarthritis," Rheumatology (Oxford) 2004, 43:321-4.
Eckhoff et al., "Difference Between the Epicondylar and Cylindrical Axis of the Knee," Clin Orthop Relat Res. 2007;461:238-44.
Eisenhart-Rothe et al., "Femorotibial and Patellar Cartilage Loss in Patients Prior to Total Knee arthroplasty, Heterogeneity, and Correlation with alignment of the Knee," Ann Rheum Dis., Jun. 2005 (BMJ Publishing Group Ltd & European League Against Rheumatism).
Eisenhart-Rothe et al., "The Role of Knee alignment in Disease Progression and Functional Decline in Knee Osteoarthritis," JAMA 2001, 286:188-95.
Elias et al., "A Correlative Study of the Geometry and anatomy of the Distal Femur," Clin orthop Relat Res. 1990(260):98-103.
Favorito et al., "total Knee Arthroplasty in the Valgus Knee," Journal Am Acad Orthop surg. 2002;10(1):16-24.
Freeman et al., "The Movement of the Knee Studied by Magnetic Resonance Imaging," Clinical orthop Relat Res. 2003(410):35-43.
Freeman et al., "The movement of the Normal Tibio-Femoral Joint," Journal Biomech. 2005;38(2):197-208.
Graichen et al., "Quantitative Assessment of Cartilage Status in Osteoarthritis by Quantitative Magnetic Resonance Imaging: Technical Validation for Use in analysis of Cartilage Volue and Further Morphologic Parameters," Arthritis Rheum 2004, 50:811-6.
Gruen et al., "Least Squares 3D Surface and Curve Matching," ISPRS Journal of Photogrammetry & Remote Sensing, 59(2005), 151-174.
Hollister et al., "The Axes of Rotation of the Knee," Clin Orthop Relat Res. 1993(290):259-68.
Howell et al., "Longitudinal Shapes of the Tibia and Femur are Unrelated and Variable," Clinical Orthopaedics and Related Research (2010) 468: 1142-1148.
Howell et al., "Results of an Initial Experience with Custom-Fit Positioning Total Knee Arthroplasty in a Series of 48 Patients," Orthopedics, 2008;31(9):857-63.
Howell et al., "In Vivo Adduction and Reverse Axial Rotation (External) of the Tibial Component can be Minimized During Standing and Kneeling," Orthopedics, In Press.
Iwaki et al., "Tibiofemoral Movement 1: The Shapes and Relative Movements of the Femur and Tibia in the Unloaded Cadaver Knee," Journal Bone Joint Surg Br. 2000;82(8):1189-95.
Jacobs et al., "Hip Resurfacing Through an Anterolateral Approach," J. Bone Joint Surg Am. 2008:90 Suppl 3:38-44.
Johnson, "Joint Remodeling as the Basis for Osteoarthritis," Journal Am Vet Med Assoc. 1962, 141:1233-41.
Kass et al., "Active Contour Models, International Journal of Computer Vision," pp. 321-331 (1988).
Kellgren et al., "Radiological Assessment of Osteoarthrosis," Ann Rheum Dis 1957, 10:494-501.
Kessler et al, "Sagittal Curvature of Total Knee Replacements Predicts in vivo Kinematics," Clin Biomech (Bristol, Avon) 2007; 22(1):52-8.
Kienzel III et al., "Total Knee Replacement," IEEE May/Jun. 1995.
Kienzel III et al., "An Integrated CAD-Robotics System for Total Knee Replacement Surgery", IEEE International Conference, pp. 889-894, vol. 1, May 1993.
Krackow et al., "Flexion-Extension Joint Gap Changes After Lateral Structure Release for Valgus Deformity Correction in Total Knee Arthroplasty: A Cadaveric Study," Journal Arthroplasty, 1999;14(8):994-1004.
Krackow et al., "Primary Total Knee Arthroplasty in Patients with Fixed Valgus Deformity," Clin Orthop Relat Res. 1991(273):9-18.
Krackow, "Approaches to Planning lower Extremity alignment for Total Knee arthroplasty and Osteotomy About the Knee," adv Orthop surg 7:69, 1983.
Lea et al., "Registration and immobilization in robot-assisted surgery", Journal of Image Guided Surgery, pp. 1-10, 1995.
Manner et al., "Knee Deformity in Congenital Longitudinal Deficiencies of the Lower Extremity," Clin Orthop Relat Res. 2006;448:185-92.
Matsuda et al., "Anatomical Analysis of the Femoral Condyle in Normal and Osteoarthritic Knees," Journal Orthopaedic Res. 2004;22(1):104-9.
Matsuda et al., "Femoral Condyle Geometry in the Normal and Varus Knee," Clinical Orthop Relat Res. 1998(349):183-8.
Messmer et al., "Volumetric Determination of the Tibia Based on 2d Radiographs Using a 2d/3d Database", Dept. of Surgery, Trauma Unit, University Hospital, Bassel, Switzerland, *Computer Aided Surgery* 6:183-194 (2001).
Mihalko et al., The Variability of Intramedullary Alignment of the Femoral Component During Total Knee Arthroplasty, Journal Arthroplasty. 2005;20(1):25-8.
Naoki Kusumoto, Taiji et al., "Application of Virtual Reality Force Feedback Haptic Device for Oral Implant Surgery", Graduate School of Dentistry Course for Integrated Oral Science and Stomatology, Jun. 16, 2005.
Panjabi et al., "Errors in Kinematic Parameters of a Planar Joint: Guidelines for Optimal Experimental Design," Journal Biomech. 1982;15(7):537-44.
Perillo-Marcone et al., "Effect of Varus/Valgus Malalignment on Bone Strains in the Proximal Tibia After TKR: An Explicit Finite element Study," Journal Biomechanical Engineering 2007, vol. 129, 1:1-11.
Peterfy et al., "Quantification of articular Cartilage in the Knee with Pulsed Saturation Transfer Subtraction and Fact-Suppressed MR Imaging: Optimization and Validation," Radiology 1994, 192:485-91.
Pinskerova et al., "The Shapes and Relative Movements of the Femur and Tibia at the Knee," Orthopaedics 2000;29 Suppl 1:S3-5.
Rosset et al., "General Consumer Communication Tools for Improved Image Management and Communication in Medicine," Journal Digital Imaging, 2005;18(4):270-9.
Shakespeare D., "Conventional Instruments in Total Knee Replacement: What Should We Do With Them?" Knee. 2006;13(1):1-6.
Shepstone et al., "The shape of the Distal Femur: A Palaeopathological Comparison of Eburnated and Non-Eburnated Femora," Ann. Rheum Dis. 1999, 58:72-8.
Siston et al., "The Variability of Femoral Rotational Alignment in Total Knee Arthroplasty," Journal Bone Joint Surg Am. 2005;87(10):2276-80.

(56) References Cited

OTHER PUBLICATIONS

Siston et al., "Averaging Different Alignment Axes Improves Femoral Rotational Alignment in Computer-Navigated Total Knee Arthroplasty," Journal Bone Joint Surg Am. 2008;90(10):2098-104.
Soudan et al., "Methods, Difficulties and Inaccuracies in the Study of Human Joint Kinematics and Pathokinematics by the Instant axis Concept. Example: The Knee Joint," Journal Biomech. 1979;12(1):27-33.
Spencer et al., "Initial Experience with Custom-Fit Total Knee Replacement: Intra-operative Events and Long-Leg Coronal alignment," International Orthopaedics (SICOT), 2009:In Press.
Stulberg et al., "Computer- and Robot-Assisted Orthopaedic Surgery", Computer-Integrated Surgery Technology and Clinical Applications, edited by Taylor et al., Massachusetts Institute of Technology, Chapter 27, pp. 373-378, 1996.
Teeny et al., "Primary Total Knee Arthroplasty in Patients with Severe Varus Deformity. A Comparative Study," Clin Orthop Relat Res. 1991(273):19-31.
Wright Medical Technology, Inc., "Prophecy Pre-Operative Naviation Guides Surgical Technique," 2009.
International Search Report and Written Opinion, International Patent Application No. PCT/US2008/083125, dated Mar. 9, 2009, 13 pages.
U.S. Appl. No. 10/146,862, (abandoned) May 15, 2002, Park et al.
U.S. Appl. No. 29/296,687, filed Oct. 25, 2007, Park.
U.S. Appl. No. 13/086,275, filed Apr. 13, 2011, Park et al.
U.S. Appl. No. 13/066,568, filed Apr. 18, 2011, Pavlovskaia.
Final Office Action, U.S. Appl. No. 11/959,344, dated Oct. 27, 2011, 12 pages.
Final Office Action, U.S. Appl. No. 12/390,667, dated Jan. 13, 2012, 27 pages.
Non-Final Office Action, U.S. Appl. No. 11/924,425, dated Jan. 25, 2012, 35 pages.
Non-Final Office Action, U.S. Appl. No. 12/386,105, dated Feb. 9, 2012, 30 pages.
Non-Final Office Action, U.S. Appl. No. 12/391,008, dated Oct. 31, 2011, 44 pages.
Notice of Allowance, U.S. Appl. No. 13/066,568, dated Oct. 26, 2011, 28 pages.
Office Action (Restriction Requirement), U.S. Appl. No. 12/563,809, dated Feb. 2, 2012, 7 pages.
Response to Final Office Action, U.S. Appl. No. 11/959,344, filed Dec. 27, 2011, 16 pages.
Response to Non-Final Office Action, U.S. Appl. No. 12/390,667, filed Nov. 18, 2011, 16 pages.
Response to Non-Final Office Action, U.S. Appl. No. 11/641,569, filed Dec. 2, 2011, 7 pages.
Response to Non-Final Office Action, U.S. Appl. No. 12/391,008, filed Feb. 24, 2012, 18 pages.
Response to Restriction Requirement, U.S. Appl. No. 12/386,105, filed Dec. 21, 2011, 9 pages.
Response to Restriction Requirement, U.S. Appl. No. 12/563,809, filed Feb. 24, 2012, 10 pages.
Response to Restriction, U.S. Appl. No. 11/924,425, filed Nov. 8, 2011, 5 pages.
Restriction Requirement, U.S. Appl. No. 11/924,425, dated Oct. 13, 2011, 6 pages.
Restriction Requirement, U.S. Appl. No. 12/386,105, dated Oct. 24, 2011, 7 pages.
Appeal Brief, U.S. Appl. No. 12/390,667, filed Jul. 12, 2012, 32 pages.
Final Office Action, U.S. Appl. No. 11/641,382, dated Jul. 25, 2012, 12 pages.
Final Office Action, U.S. Appl. No. 11/924,425, dated Jul. 6, 2012, 14 pages.
Non-Final Office Action, U.S. Appl. No. 12/111,924, dated Jun. 29, 2012, 35 pages.
Non-Final Office Action, U.S. Appl. No. 12/546,545, dated Jul. 19, 2012, 28 pages.
Non-Final Office Action, U.S. Appl. No. 12/636,939, dated Jul. 20, 2012, 25 pages.
Non-Final Office Action, U.S. Appl. No. 13/374,960, dated Aug. 1, 2012, 6 pages.
Notice of Allowance, U.S. Appl. No. 12/386,105, dated Jul. 5, 2012, 11 pages.
Response to Final Office Action, U.S. Appl. No. 11/641,569, filed Jun. 28, 2012, 10 pages.
Response to Non-Final Office Action, U.S. Appl. No. 12/386,105, filed Jun. 8, 2012, 13 pages.
Response to Non-Final Office Action, U.S. Appl. No. 11/641,382, filed Jun. 27, 2012, 12 pages.
Response to Restriction, U.S. Appl. No. 12/563,809, filed Aug. 6, 2012, 10 pages.
Response to Restriction, U.S. Appl. No. 12/546,545, filed Jun. 4, 2012, 7 pages.
Restriction Requirement, U.S. Appl. No. 12/563,809, dated Jul. 6, 2012, 6 pages.
U.S. Appl. No. 13/488,505, filed Jun. 5, 2012, Ilwhan Park et al.
U.S. Appl. No. 13/573,662, filed Oct. 2, 2012, Pavlovskaia et al.
U.S. Appl. No. 13/723,904, filed Dec. 21, 2012, Park.
U.S. Appl. No. 13/730,467, filed Dec. 28, 2012, Park et al.
U.S. Appl. No. 13/730,585, filed Dec. 28, 2012, Park et al.
U.S. Appl. No. 13/730,608, filed Dec. 28, 2012, Park et al.
U.S. Appl. No. 13/731,697, filed Dec. 31, 2012, Pavlovskaia et al.
U.S. Appl. No. 13/731,850, filed Dec. 31, 2012, Park.
U.S. Appl. No. 13/749,095, filed Jan. 24, 2013, Song.
Advisory Action and Interview Summary, U.S. Appl. No. 12/390,667, dated Apr. 27, 2012, 23 pages.
Final Office Action, U.S. Appl. No. 11/641,569, dated Mar. 1, 2012, 12 pages.
Final Office Action, U.S. Appl. No. 12/391,008, dated May 17, 2012, 28 pages.
Non-Final Office Action, U.S. Appl. No. 11/641,382, dated Mar. 29, 2012, 24 pages.
Notice of Allowance, U.S. Appl. No. 11/959,344, dated Mar. 5, 2012, 13 pages.
Response to Final Office Action, U.S. Appl. No. 12/390,667, filed Mar. 12, 2012, 19 pages.
Response to Non-Final Office Action, U.S. Appl. No. 11/924,425, filed Apr. 25, 2012, 8 pages.
Response to Restriction Requirement, U.S. Appl. No. 12/111,924, filed Apr. 16, 2012, 8 pages.
Response to Restriction Requirement, U.S. Appl. No. 12/636,939, filed Apr. 19, 2012, 6 pages.
Response to Restriction, U.S. Appl. No. 12/505,056, filed Apr. 11, 2012, 9 pages.
Restriction Requirement, U.S. Appl. No. 12/111,924, dated Mar. 19, 2012, 8 pages.
Restriction Requirement, U.S. Appl. No. 12/505,056, dated Mar. 14, 2012, 8 pages.
Restriction Requirement, U.S. Appl. No. 12/546,545, dated May 3, 2012, 8 pages.
Restriction Requirement, U.S. Appl. No. 12/636,939, dated Apr. 13, 2012, 6 pages.
Amendment Under 37 C.F.R. 1.312, U.S. Appl. No. 12/386,105, filed Oct. 1, 2012, 6 pages.
Appeal Brief, U.S. Appl. No. 12/391,008, filed Oct. 16, 2012, 24 pages.
Examiner's Answer in appeal, U.S. Appl. No. 12/391,008, dated Dec. 13, 2012, 27 pages.
Final Office Action, U.S. Appl. No. 12/546,545, dated Dec. 20, 2012, 16 pages.
Final Office Action, U.S. Appl. No. 12/636,939, dated Jan. 25, 2013, 9 pages.
Howell et al., "In Vivo Adduction and Reverse Axial Rotation (External) of the Tibial Component can be Minimized During Standing and Kneeling," Orthopedics|ORTHOSupersite.com vol. 32 No. 5, 319-326 (May 2009).
Non-Final Office Action, U.S. Appl. No. 11/641,569, dated Jan. 3, 2013, 12 pages.
Non-Final Office Action, U.S. Appl. No. 13/086,275, dated Feb. 7, 2013, 36 pages.

(56) References Cited

OTHER PUBLICATIONS

Non-Final Office Action, U.S. Appl. No. 12/390,667, dated Sep. 26, 2012, 21 pages.
Non-Final Office Action, U.S. Appl. No. 12/563,809, dated Sep. 21, 2012, 32 pages.
Notice of Allowance, U.S. Appl. No. 11/641,382, dated Feb. 6, 2013, 14 pages.
Notice of Allowance, U.S. Appl. No. 11/924,425, dated Feb. 5, 2013, 16 pages.
Notice of Allowance, U.S. Appl. No. 12/111,924, dated Dec. 24, 2012, 10 pages.
Notice of Allowance, U.S. Appl. No. 29/394,882, dated Feb. 4, 2013, 32 pages.
Notice of Allowance, U.S. Appl. No. 11/641,382, dated Oct. 9, 2012, 9 pages.
Notice of Allowance, U.S. Appl. No. 11/924,425, dated Sep. 25, 2012, 18 pages.
Notice of Allowance, U.S. Appl. No. 13/374,960, dated Nov. 2, 2012, 24 pages.
Response to Final Office Action, U.S. Appl. No. 11/641,382, filed Sep. 24, 2012, 11 pages.
Response to Final Office Action, U.S. Appl. No. 11/924,425, filed Sep. 5, 2012, 9 pages.
Response to Non-Final Office Action, U.S. Appl. No. 12/563,809, filed Dec. 13, 2012, 15 pages.
Response to Non-Final Office Action, U.S. Appl. No. 12/111,924, filed Sep. 28, 2012, 10 pages.
Response to Non-Final Office Action, U.S. Appl. No. 12/636,939, filed Oct. 10, 2012, 8 pages.
Response to Non-Final Office Action, U.S. Appl. No. 12/546,545, filed Oct. 19, 2012, 15 pages.
Response to Restriction, U.S. Appl. No. 13/573,662, filed Feb. 8, 2013, 8 pages.
Restriction Requirement, U.S. Appl. No. 13/573,662, dated Jan. 17, 2013, 6 pages.
U.S. Appl. No. 13/923,093, filed Jun. 20, 2013, Park.
U.S. Appl. No. 13/960,498, filed Aug. 6, 2013, Song.
U.S. Appl. No. 14/011,998, filed Aug. 28, 2013, Park et al.
U.S. Appl. No. 14/084,255, filed Nov. 19, 2013, Park et al.
U.S. Appl. No. 14/086,849, filed Nov. 21, 2013, Park et al.
U.S. Appl. No. 14/086,878, filed Nov. 21, 2013, Park et al.
Amendment Under 37 C.F.R. 1.312, U.S. Appl. No. 13/374,960, filed May 7, 2013, 6 pages.
Audette et al. "An algorithmic overview of surface registration techniques for medical imaging." Medical Image Analysis, vol. 4, No. 3, Sep. 1, 2000, pp. 201-217.
European Search Report, EP09739422.5, dated Mar. 28, 2013, 9 pages.
Final Office Action, U.S. Appl. No. 12/390,667, dated Oct. 25, 2013, 17 pages.
Final Office Action, U.S. Appl. No. 12/546,545, dated Oct. 7, 2013, 24 pages.
Final Office Action, U.S. Appl. No. 12/563,809, dated Mar. 7, 2013, 14 pages.
Ibanez et al., The ITK Software Guide, Second Edition, Updated for ITK version 2.4, Nov. 21, 2005, pp. 114, 396-411, and 426.
Non-Final Office Action, U.S. Appl. No. 11/641,569, dated Jul. 12, 2013, 21 pages.
Non-Final Office Action, U.S. Appl. No. 11/642,385, dated Oct. 22, 2013, 37 pages.
Non-Final Office Action, U.S. Appl. No. 11/656,323, dated Oct. 22, 2013, 36 pages.
Non-Final Office Action, U.S. Appl. No. 12/390,667, dated May 8, 2013, 20 pages.
Non-Final Office Action, U.S. Appl. No. 12/505,056, dated Jun. 28, 2013, 7 pages.
Non-Final Office Action, U.S. Appl. No. 12/546,545, dated Mar. 13, 2013, 10 pages.
Non-Final Office Action, U.S. Appl. No. 12/636,939, dated Apr. 25, 2013, 16 pages.
Non-Final Office Action, U.S. Appl. No. 12/760,388, dated Jun. 20, 2013, 54 pages.
Non-Final Office Action, U.S. Appl. No. 13/723,904, dated Aug. 9, 2013, 6 pages.
Non-Final Office Action, U.S. Appl. No. 13/730,585, dated Jun. 11, 2013, 10 pages.
Non-Final Office Action, U.S. Appl. No. 13/730,608, dated Oct. 7, 2013, 10 pages.
Notice of Allowance, Design U.S. Appl. No. 29/394,882, dated May 24, 2013, 16 pages.
Notice of Allowance, U.S. Appl. No. 12/111,924, dated Mar. 11, 2013, 14 pages.
Notice of Allowance, U.S. Appl. No. 12/563,809, dated May 28, 2013, 11 pages.
Notice of Allowance, U.S. Appl. No. 12/636,939, dated Oct. 7, 2013, 28 pages.
Notice of Allowance, U.S. Appl. No. 13/086,275, dated Aug. 27, 2013, 31 pages.
Notice of Allowance, U.S. Appl. No. 13/374,960, dated May 6, 2013, 20 pages.
Notice of Allowance, U.S. Appl. No. 13/573,662, dated Mar. 19, 2013, 34 pages.
Preliminary Amendment, U.S. Appl. No. 13/731,697, filed May 10, 2013, 6 pages.
Response to Final Office Action, U.S. Appl. No. 12/546,545, filed Feb. 20, 2013, 13 pages.
Response to Final Office Action, U.S. Appl. No. 12/563,809, filed May 6, 2013, 15 pages.
Response to Final Office Action, U.S. Appl. No. 12/636,939, filed Apr. 8, 2013, 10 pages.
Response to Non-Final Office Action, U.S. Appl. No. 12/390,667, filed Feb. 26, 2013, 36 pages.
Response to Non-Final Office Action, U.S. Appl. No. 11/641,569, filed Apr. 3, 2013, 9 pages.
Response to Non-Final Office Action, U.S. Appl. No. 13/086,275, filed May 7, 2013, 11 pages.
Response to Non-Final Office Action, U.S. Appl. No. 12/546,545, filed Jul. 15, 2013, 14 pages.
Response to Non-Final Office Action, U.S. Appl. No. 12/636,939, filed Jul. 16, 2013, 15 pages.
Response to Non-Final Office Action, U.S. Appl. No. 12/390,667, filed Aug. 7, 2013, 22 pages.
Response to Non-Final Office Action, U.S. Appl. No. 12/760,388, filed Sep. 12, 2013, 15 pages.
Response to Non-Final Office Action, U.S. Appl. No. 12/505,056, filed Oct. 9, 2013, 17 pages.
Response to Non-Final Office Action, U.S. Appl. No. 13/730,585, filed Oct. 9, 2013, 15 pages.
Response to Non-Final Office Action, U.S. Appl. No. 11/641,569, filed Oct. 11, 2013, 12 pages.
Response to Non-Final Office Action, U.S. Appl. No. 13/723,904, filed Nov. 6, 2013, 8 pages.
Response to Restriction Requirement, U.S. Appl. No. 12/760,388, filed Apr. 5, 2013, 7 pages.
Restriction Requirement, U.S. Appl. No. 12/760,388, dated Mar. 6, 2013, 7 pages.
Xie et al. "Segmentation by surface-to-image registration." proceedings of SPIE, vol. 6144, Mar. 2 2006, pp. 614405-1-614405-7.
U.S. Appl. No. 14/272,147, filed May 7, 2014, Park et al.
Extended European search Report, European Appl. No. 08863202.1, dated May 16, 2014.
Extended European search Report, European Appl. No. 13188389.4, dated Jan. 8, 2014.
Final Office Action, U.S. Appl. No. 11/641,569, dated Nov. 29, 2013, 20 pages.
Final Office Action, U.S. Appl. No. 11/642,385, dated Apr. 25, 2014.
Final Office Action, U.S. Appl. No. 11/656,323, dated Apr. 3, 2014.
Final Office Action, U.S. Appl. No. 12/505,056, dated Dec. 30, 2013, 48 pages.
Final Office Action, U.S. Appl. No. 13/723,904, dated Dec. 24, 2013, 10 pages.
Final Office Action, U.S. Appl. No. 13/730,585, dated Dec. 27, 2013, 8 pages.

(56) References Cited

OTHER PUBLICATIONS

Japanese Office Action, JP Application No. 2011-507530, dated Dec. 17, 2013, 8 pages.
Non-Final Office Action, U.S. Appl. No. 13/730,467, dated Jan. 15, 2014, 8 pages.
Notice of Allowance, U.S. Appl. No. 11/641,569, dated Feb. 5, 2014, 11 pages.
Notice of Allowance, U.S. Appl. No. 12/390,667, dated Jan. 17, 2014, 9 pages.
Notice of Allowance, U.S. Appl. No. 12/505,056, dated Mar. 6, 2014, 10 pages.
Notice of Allowance, U.S. Appl. No. 12/546,545, dated Dec. 26, 2013, 9 pages.
Notice of Allowance, U.S. Appl. No. 12/760,388, dated Jan. 22, 2014, 13 pages.
Notice of Allowance, U.S. Appl. No. 13/723,904, dated Mar. 7, 2014, 8 pages.
Notice of Allowance, U.S. Appl. No. 13/730,467, dated May 5, 2014.
Notice of Allowance, U.S. Appl. No. 13/730,585, dated Mar. 18, 2014, 10 pages.
Notice of Allowance, U.S. Appl. No. 13/730,608, dated Apr. 18, 2014.
Notice of Allowance, U.S. Appl. No. 13/731,850, dated Jun. 6, 2014.
Preliminary Amendment, U.S. Appl. No. 13/731,850, filed Apr. 11, 2014, 8 pages.
Response to Final Office Action, U.S. Appl. No. 11/641,569, dated Jan. 29, 2014, 10 pages.
Response to Final Office Action, U.S. Appl. No. 12/390,667, dated Dec. 23, 2013, 5 pages.
Response to Final Office Action, U.S. Appl. No. 12/546,545, dated Dec. 9, 2013, 8 pages.
Response to Final Office Action, U.S. Appl. No. 12/505,056, dated Feb. 26, 2014, 19 pages.
Response to Final Office Action, U.S. Appl. No. 13/723,904, dated Feb. 19, 2014, 7 pages.
Response to Final Office Action, U.S. Appl. No. 13/730,585, dated Feb. 26, 2014, 9 pages.
Response to Non-Final Office Action, U.S. Appl. No. 13/730,608, dated Jan. 7, 2014, 16 pages.
Response to Non-Final Office Action, U.S. Appl. No. 11/656,323, dated Jan. 17, 2014, 10 pages.
Response to Non-Final Office Action, U.S. Appl. No. 11/642,385, dated Feb. 24, 2014, 16 pages.
Response to Non-Final Office Action, U.S. Appl. No. 13/730,467, dated Apr. 11, 2014, 8 pages.
Response to Restriction, U.S. Appl. No. 13/488,505, dated May 5, 2014, 7 pages.
Restriction Requirement, U.S. Appl. No. 13/488,505, dated Mar. 4, 2014, 5 pages.
Supplementary European Search Report and Opinion, EP 09739474.6, dated Feb. 27, 2014, 7 pages.
Advisory Action, U.S. Appl. No. 11/642,385, dated Aug. 1, 2014.
Amendment and Response After Final Office Action, U.S. Appl. No. 11/656,323, dated Aug. 25, 2014.
Appeal Brief, U.S. Appl. No. 11/642,385, dated Oct. 7, 2014.
Canadian Office Action, Appl. No. 2708393, dated Jul. 29, 2014.
European Search Report, EP 09835583.7, dated May 9, 2014.
European Search Report, EP09823986.6, dated Sep. 23, 2014.
International Search Report and Written Opinion, PCT/US2014/030496, dated Aug. 6, 2014.
Non-Final Office Action, U.S. Appl. No. 11/656,323, dated Sep. 18, 2014.
Non-Final Office Action, U.S. Appl. No. 13/488,505, dated Jul. 17, 2014.
Response to Final Office Action, U.S. Appl. No. 11/642,385, dated Jul. 22, 2014.
Response to Restriction, U.S. Appl. No. 13/749,095, dated Nov. 13, 2014.
Restriction Requirement, U.S. Appl. No. 13/749,095, dated Sep. 25, 2014.
Banks et al. "Accurate Measurement of Three-Dimensional Knee Replacement Kinematics Using Single-Plane Fluoroscopy." *IEEE Transactions on Biomedical Engineering*, vol. 43, No. 6, Jun. 1996.
Delp et al. "An Interactive Graphics-Based Model of the lower Extremity to Study Orthopaedic Surgical Procedures." *IEEE Transactions on Biomedical Engineering*, vol. 37, No. 8, Aug. 1990.
Garg, A. et al., "Prediction of Total Knee Motion Using a Three-Dimensional Computer-Graphics Model." *J. Biomechanics*, vol. 23, No. 1, pp. 45-58, 1990.
Walker, P. S. et al. "Range of Motion in Total Knee Arthroplasty: A Computer Analysis." *Clinical Orthopaedics and Related Research*, No. 262, Jan. 1991.
Australian Patent Examination Report No. 1, AU 2013200861, dated Mar. 3, 2015.
Canadian Office Action, Appl. No. 2642616, dated Apr. 22, 2015.
Canadian Office Action, CA2708393, dated May 7, 2015.
Canadian Office Action, CA2721735, dated Jul. 7, 2015.
European Examination Report, EP10192631.9, dated Feb. 11, 2015.
European Search Report, EP09718014.5, dated May 13, 2015.
European Search Report, EP09718041.8, dated May 12, 2015.
Japanese Office Action, JP2014-147908, dated Jun. 9, 2015.
Non-Final Office Action, U.S. Appl. No. 13/731,697, dated Jan. 29, 2015.
Non-Final Office Action, U.S. Appl. No. 13/749,095, dated Jan. 27, 2015.
Non-Final Office Action, U.S. Appl. No. 14/476,500, dated Jun. 18, 2015.
Notice of Allowance, U.S. Appl. No. 11/656,323, dated Feb. 3, 2015.
Notice of Allowance, U.S. Appl. No. 13/731,697, dated Jul. 29, 2015.
Reply Brief, U.S. Appl. No. 11/642,385, dated Jan. 23, 2015.
Response to Non-Final Office Action, U.S. Appl. No. 13/731,697, dated May 26, 2015.
Response to Non-Final Office Action, U.S. Appl. No. 13/749,095, dated Apr. 20, 2015.
Response to Restriction, U.S. Appl. No. 14/476,500, dated Mar. 17, 2015.
Restriction Requirement, U.S. Appl. No. 14/476,500, dated Feb. 25, 2015.
Richolt et al. "Planning and Evaluation of Reorienting Osteotomies of the Proximal Femur in Cases of SCFE Using Virtual Three-Dimensional Models." *Lecture Notes in Computer Science*, vol. 1496, 1998, pp. 1-8.
Amendment Under 37 CFR 1.312, U.S. Appl. No. 14/824,731, dated Dec. 28, 2015.
Canadian Office Action, CA2721762, dated Nov. 10, 2015.
Decision on Appeal, U.S. Appl. No. 12/391,008, dated Dec. 11, 2015.
EP Communication pursuant to Article 94(3) EPC, EP10192631.9, dated Feb. 12, 2016.
European Patent Office, Summons to Attend Oral Proceedings, EP07749030.8, dated Sep. 10, 2015.
Final Rejection, U.S. Appl. No. 13/749,095, dated Dec. 24, 2015.
Final Rejection, U.S. Appl. No. 14/476,500, dated Feb. 1, 2016.
Non-Final Office Action, U.S. Appl. No. 13/749,095, dated Sep. 10, 2015.
Non-Final Office Action, U.S. Appl. No. 13/923,093, dated Dec. 2, 2015.
Non-Final Office Action, U.S. Appl. No. 13/960,498, dated Feb. 9, 2016.
Non-Final Office Action, U.S. Appl. No. 14/011,998, dated Feb. 12, 2016.
Non-Final Office Action, U.S. Appl. No. 14/084,255, dated Feb. 25, 2016.
Notice of Allowance, U.S. Appl. No. 12/391,008, dated Dec. 22, 2015.
Notice of Allowance, U.S. Appl. No. 14/824,731, dated Oct. 20, 2015.
Response to Final Office Action, U.S. Appl. No. 13/749,095, dated Feb. 17, 2016.

(56) References Cited

OTHER PUBLICATIONS

Response to Non-Final Office Action, U.S. Appl. No. 14/476,500, dated Oct. 16, 2015.
Response to Restriction, U.S. Appl. No. 13/960,498, dated Nov. 19, 2015.
Restriction Requirement, U.S. Appl. No. 13/960,498, dated Sep. 23, 2015.
Canadian Office Action, CA2642616, dated Feb. 26, 2016.
Canadian Office Action, CA2708393, dated Mar. 11, 2016.
Canadian Office Action, CA2721762, dated Jul. 20, 2016.
EP Search Report and Opinion, EP09800841.0, dated Mar. 22, 2016.
Final Office Action, U.S. Appl. No. 13/923,093, dated Jul. 14, 2016.
Final Office Action, U.S. Appl. No. 14/011,998, dated Jul. 14, 2016.
Final Office Action, U.S. Appl. No. 14/084,255, dated Jul. 26, 2016.
Non-Final Office Action, U.S. Appl. No. 14/272,147, dated Jun. 17, 2016.
Non-Final Office Action, U.S. Appl. No. 14/869,762, dated Mar. 31, 2016.
Non-Final Office Action, U.S. Appl. No. 14/946,106, dated Jun. 23, 2016.
Non-Final Office Action, U.S. Appl. No. 15/168,405, dated Aug. 3, 2016.
Notice of Allowance, U.S. Appl. No. 13/749,095, dated Apr. 7, 2016.
Notice of Allowance, U.S. Appl. No. 14/476,500, dated May 19, 2016.
Response to Non-Final Office Action, U.S. Appl. No. 13/923,093, dated May 2, 2016.
Response to Non-Final Office Action, U.S. Appl. No. 14/011,998, dated May 6, 2016.
Response to Non-Final Office Action, U.S. Appl. No. 14/084,255, dated May 23, 2016.
Response to Non-Final Office Action, U.S. Appl. No. 14/869,762, dated Jun. 29, 2016.
Restriction Requirement, U.S. Appl. No. 14/335,431, dated Aug. 12, 2016.
Taylor et al., "Computer-integrated revision total hip replacement surgery: concept and preliminary results," Medical Image Analysis (1999) vol. 3, No. 3, pp. 301-319.

* cited by examiner

GENERATING MRI IMAGES USABLE FOR THE CREATION OF 3D BONE MODELS EMPLOYED TO MAKE CUSTOMIZED ARTHROPLASTY JIGS

FIELD OF THE INVENTION

The present invention relates to medical imaging. More specifically, the present invention relates to medical imaging employed to generate three-dimensional bone models for use in the creation of customized arthroplasty jigs.

BACKGROUND OF THE INVENTION

Systems and methods for making customized arthroplasty jigs are disclosed in these three U.S. patent applications: U.S. patent application Ser. No. 11/656,323 to Park et al., titled "Arthroplasty Devices and Related Methods" and filed Jan. 19, 2007; U.S. patent application Ser. No. 10/146,862 to Park et al., titled "Improved Total Joint Arthroplasty System" and filed May 15, 2002; and U.S. patent Ser. No. 11/642,385 to Park et al., titled "Arthroplasty Devices and Related Methods" and filed Dec. 19, 2006. The disclosures of these three U.S. patent applications are incorporated by reference in their entireties into the present patent application.

As explained in U.S. patent application Ser. No. 11/656,323, a medical imaging system (e.g., a magnetic resonance imaging ("MRI") system, a computed tomography ("CT") system, etc.) is employed to generate multiple two-dimensional ("2D") images of a joint region of a patient. The multiple 2D images or image slices of the patient's joint region are compiled via a computer program into three-dimensional ("3D") bone and/or bone-cartilage models for use in creating customized arthroplasty jigs.

Creating the 2D images or image slices via CT imaging is relatively quick, but involves multiple scans, thus increasing the dose of radiation to a patient. Also, CT imaging requires the use of a contrast agent, which may cause an adverse reaction in some patients. Finally, CT imaging does not provide the image resolution offered by MRI.

MRI provides preferred resolution, as compared to CT imaging, allowing for the examination of soft tissue changes associated with OA, including changes to cartilage, bone, ligaments, meniscus, etc. Recent advances in MRI technology have enabled researchers to evaluate cartilage damage and progression over the cross-sectional and longitudinal planes of a joint. Unlike CT imaging, MRI involves no radiation dose.

Unfortunately, conventional MRI is not quick, requiring a patient to maintain a position completely still for 30, 45 or more minutes in order to obtain image slices that have adequate resolution. It is often extremely difficult, if not impossible, for a patient to remain completely still in any position, much less one that is often unnatural and/or difficult to maintain because of pain, fatigue, tremors and/or age.

Because of the difficulty in maintaining a position without movement for the long time period needed to obtain MRI image slices that are of adequate resolution for 3D modeling purposes, the MRI process often has to be repeated for a patient. Repeating the MRI process increases costs associated with making customized arthroplasty jigs and the lead-time needed for the manufacture of the customized arthroplasty jigs before performing the arthroplasty procedure.

There is a need in the art for a MRI system and method that improves the likelihood a MRI procedure will result in MRI image slices that are useable for the generation of 3D bone models used in the generation of customized arthroplasty jigs.

SUMMARY

Disclosed herein is a method of creating a customized arthroplasty jig. In one embodiment, the method includes: generating two-dimensional MRI images of a patient's joint area to undergo arthroplasty, wherein the MRI images are between approximately 128×128 to approximately 1024×1024 resolution and between approximately 1 mm and approximately 4 mm spacing (i.e., "hardware" spacing); generating a three-dimensional bone image of at least a portion of a bone of the patient's joint area from the generated two-dimensional MRI images; using the three-dimensional bone image to generate data pertaining to the customized arthroplasty jig, wherein the data includes bone surface information; providing the data to at least one manufacturing device; and employing the bone surface information to cause the at least one manufacturing device to create a surface on the arthroplasty jig configured to matingly receive a surface of the bone.

Disclosed herein is a method of creating a customized arthroplasty jig. In one embodiment, the method includes: generating two-dimensional MRI images of a patient's joint area to undergo arthroplasty; electronically orienting the two-dimensional MRI image slices to account for the patient's joint area being randomly physically oriented in a scanning area of a MRI machine; generating a three-dimensional bone image of at least a portion of a bone of the patient's joint area from the generated two-dimensional MRI images; using the three-dimensional bone image to generate data pertaining to the customized arthroplasty jig, wherein the data includes bone surface information; providing the data to at least one manufacturing device; and employing the bone surface information to cause the at least one manufacturing device to create a surface on the arthroplasty jig configured to matingly receive a surface of the bone.

Disclosed herein is a method of creating a customized arthroplasty jig. In one embodiment the method includes: generating a coronal MRI image of a knee joint area to undergo arthroplasty, wherein the coronal MRI image depicts a most distal point on a femur medial condyle and a most distal point on a femur lateral condyle; extending a first tangent line to intersect the distal points; generating an axial MRI image of the knee joint area, wherein the axial MRI image depicts a most posterior point on the femur medial condyle and a most posterior point on the femur lateral condyle; generating two-dimensional MRI images of the knee joint area, wherein the two-dimensional MRI images are generally perpendicular to the first and second tangent lines; generating a three-dimensional bone image of at least a portion of a bone of the patient's joint area from the generated two-dimensional MRI images; using the three-dimensional bone image to generate data pertaining to the customized arthroplasty jig; providing the data to at least one manufacturing device; and employing the data to cause the at least one manufacturing device to create the arthroplasty jig.

Disclosed herein are customized arthroplasty jigs. In one embodiment, the customized arthroplasty jigs are those made according to any of the aforementioned methods.

Disclosed herein is a method of orienting MRI slice images of a bone. In one embodiment, the method includes: generating a first MRI bone image; causing a first reference line to intersect first and second points on the first MRI bone image; and generating the MRI slice images to be generally perpendicular to the first reference line.

Disclose herein is a method of medically imaging a bone with a MRI machine. In one embodiment, the method includes: generating two-dimensional MRI images of the bone; electronically orienting the two-dimensional MRI images to account for the bone being randomly physically oriented in a scanning area of the MRI machine; running an orientation check to determine if the two-dimensional MRI images have been adequately electronically oriented; and running a motion check to determine if the excessive patient motion occurred during the generation of the two-dimensional MRI images.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION

Disclosed herein is a system and method for generating 2D MRI image slices 10 that are readily and reliably useable in creating 3D bone models 15 used in the generation of customized arthroplasty jigs 20. A MRI image resolution and MRI image slice spacing $S_S$ disclosed herein significantly reduce the time required to generate a series of MRI images slices 10, thereby making it possible for a patient 22 to maintain a position completely still for the duration of the MRI imaging process. An image slice orientation method disclosed herein ensures the 2D MRI image slices 10 are readily and reliably useable with a 3D computer modeling program to create 3D bone models 15 used in the generation of customized arthroplasty jigs 20.

Figure 1:
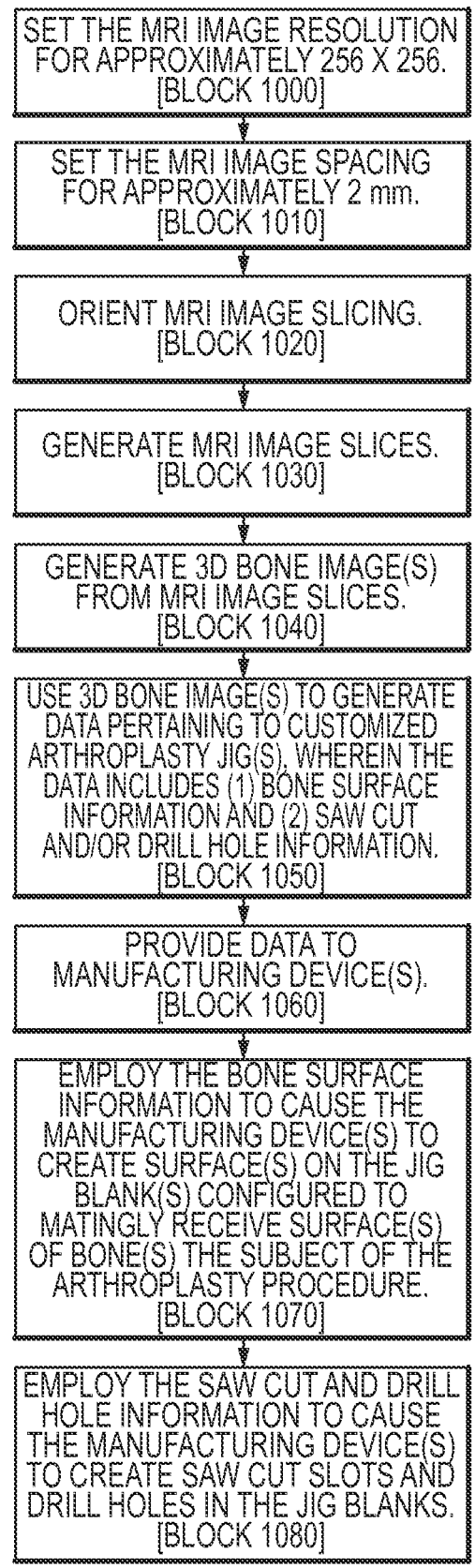
FIG. 1 is a flow chart illustrating a method of creating customized arthroplasty jigs for mating with surfaces of bones of a patient's joint targeted for arthroplasty.
Figure 2:
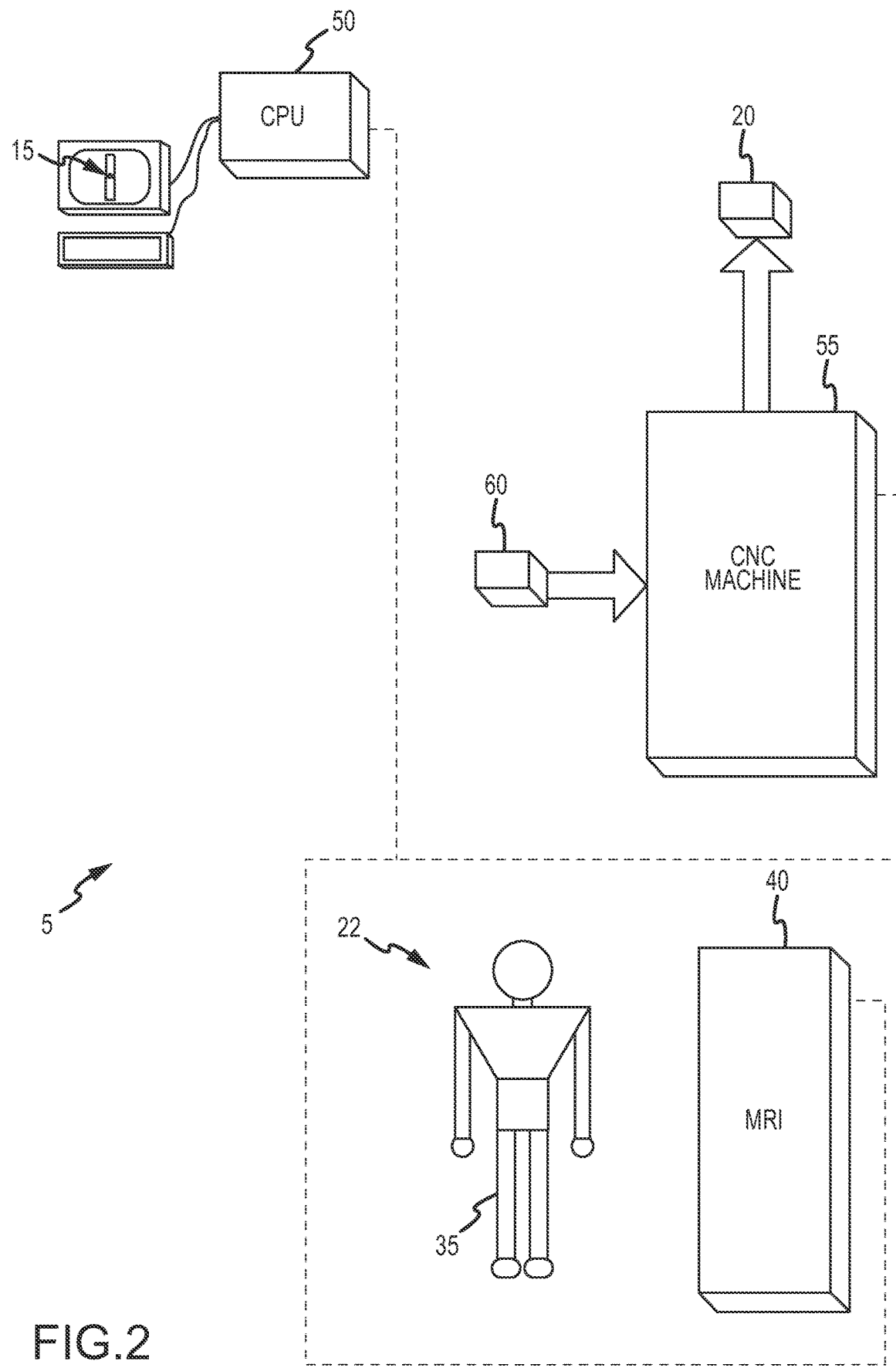
FIG. 2 is a schematic diagram of the method reflected in FIG. 1.

For a discussion of the overall process of turning MRI image slices 10 into a customized arthroplasty jig 20, reference is made to FIGS. 1 and 2. FIG. 1 is a flow chart illustrating a method of creating customized arthroplasty jigs 20 for mating with surfaces 25 of bones 30 of a patient's joint 35 targeted for arthroplasty. FIG. 2 is a schematic diagram of the method reflected in FIG. 1.

As can be understood from FIGS. 1 and 2, in one embodiment, the MRI image resolution for a MRI imaging machine 40 is set between approximately 128×128 and approximately 1024×1024. Preferably, the MRI image resolution for the MRI machine 40 may be set for approximately 256×256 [block 1000]. Image resolutions significantly higher than 256×256 (e.g., higher than 1024×1024) result in imaging times that are too long for most patients 22 to hold a position without moving, and image resolutions significantly lower than 256×256 (e.g., lower than 128×128) result in insufficient image resolution for the purposes of generating 3D bone model images 15.

MRI can provide image analysis for a variety of bone and tissue types for OA patients. For example, MRI can provide image analysis for cortical and cancellous bone and tissues such as cartilage, meniscus, and ligaments. As indicated later in this Detailed Description, in one embodiment, the MRI analysis is taken around the bone component and, more specifically, the cortical-cancellous bone edge.

MRI projects protons into the portion of the human anatomy that is the subject of the MRI. In doing so, MRI is able to measure the water volume for each of the many pixels representing the portion of the anatomy that is the subject of the MRI. In one embodiment, a pixel will be 0.3 mm×0.3 mm×2 mm in a 256×256 plane.

Because MRI only measures the water content (i.e., water volume) within each pixel and a single pixel may correspond to a location within the patient having multiple types of bone and/or tissue material, a single pixel may only represent the average water volume of the bone and/or tissue material represented by the pixel. In other words, the water volume of a single pixel is the average water content of the bone and/or tissue material represented by the pixel. Such water volume averaging for a pixel is called volume-averaging.

A single MRI pixel may represent only cortical bone (so the water volume is nearly zero percent and the image is nearly black), mixed portions of cortical and cancellous bone (so the water volume is between zero percent and 100 percent and the image color is approximately gray), or pure cancellous bone coupled with tissue (so the water volume is nearly 100 percent and the image color is white).

Where a single pixel represents more than a single bone and/or tissue type, the MRI cannot detect or differentiate between the types and amounts of bone and/or tissue represented by the single pixel. For example, where the single pixel represents a portion of the anatomy having both cortical and cancellous bone, the MRI cannot detect or differentiate between the cortical and cancellous bone types of the pixel because of the water volume averaging used for the pixel. The inability to differentiate between the bone types represented by the individual pixel is a result the volume averaging data for the single pixel being taken from the center of the water volume for the pixel, which is only the average water value and does not represent the true value of the components inside the pixel (e.g., average water volume of the single pixel does not indicate the exact portion/value for each of the cortical & cancellous bone). Therefore, the volume-averaging data cannot be called reliable and the resulting errors are not ignorable.

Figure 15:
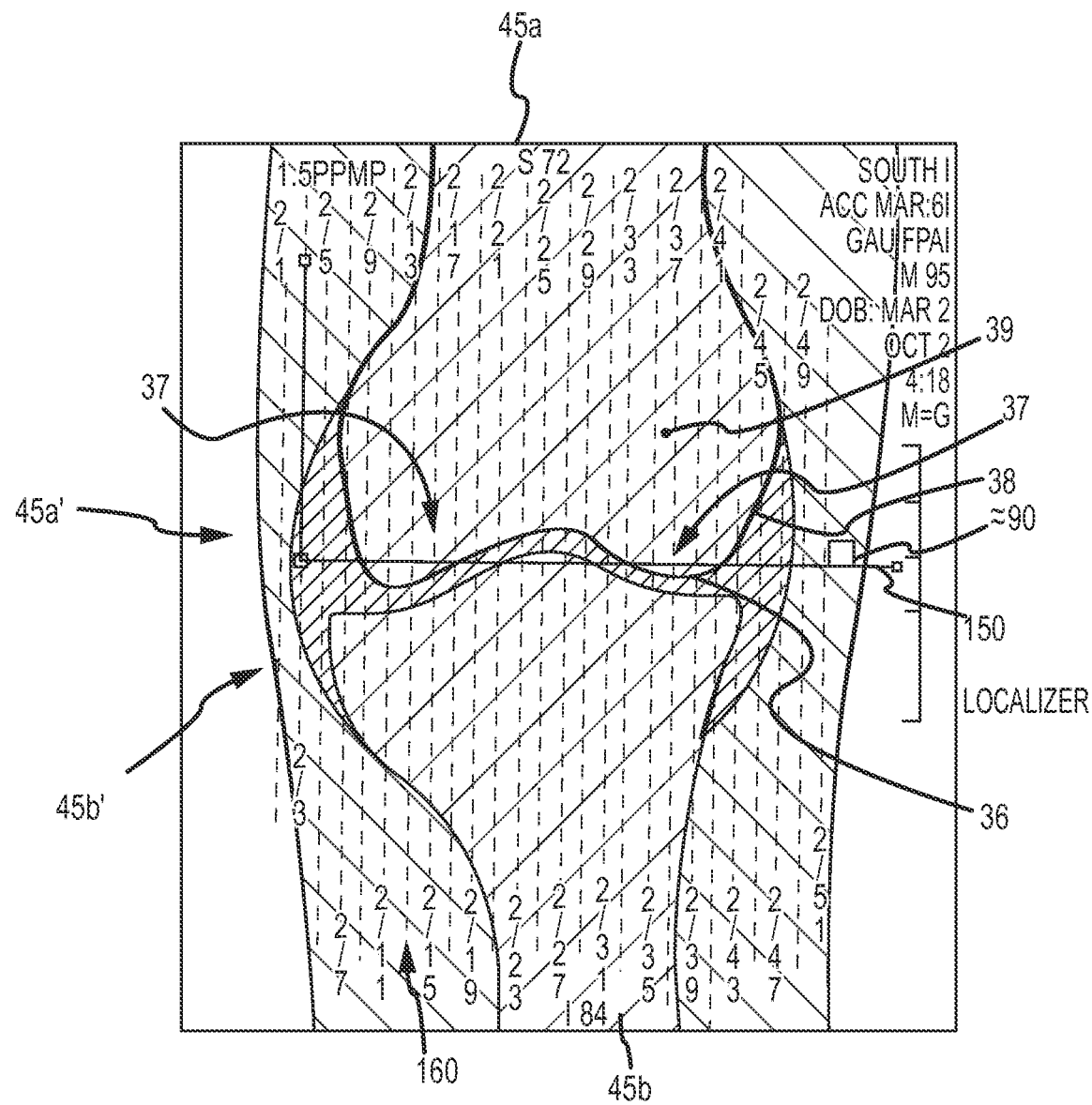
FIGS. 15 and 16 are, respectively, coronal and axial MRI image views illustrating the application of the condyle intersecting lines to electronically orient the sagittal MRI image slices.
Figure 16:
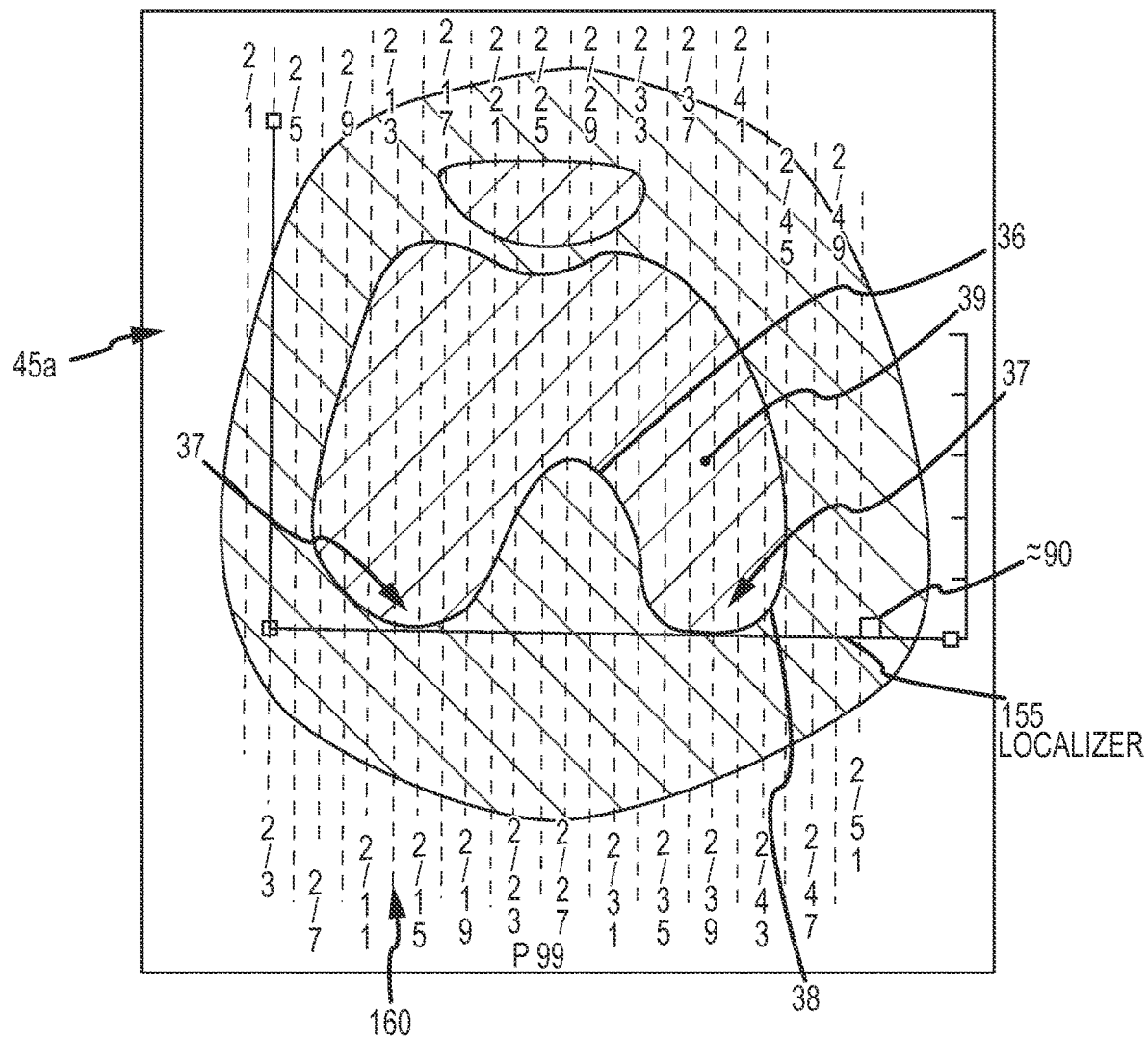

As can be understood from FIGS. 15 and 16, which are, respectively, a coronal MRI view of a femur 45a and tibia 45b of a human knee and an axial MRI view of the human knee in 90-degree extension showing the distal surfaces of the condyles 37 of the femur distal end 45a', the volume-averaging data is approximately constant in certain areas of the distal femur 45a', such as the cortical-cancellous edges 36 of the posterior femoral condyles 37. As shown in FIG. 16, a near black contour 36 extends around the posterior edges of the femoral condyles 37, where the near-black edges cover most of the cortical bone 38. A similar near black contour 36 can be seen in FIG. 15 for the cortical bone 38.

In most cases, OA damage occurs mostly in the cortical bone 38 and adjacent cartilage, and not in the cancellous bone 39. Therefore, in one embodiment, the surface area of interest for the 2D images 10 to be used to form the computer generated 3D bone models 15 is the cortical-cancellous interfaces 36 representing the edges 36 of the posterior femoral condyles 37.

In one embodiment, the MRI image slice spacing $S_S$ may be a "hardware" spacing set between approximately 1 mm and approximately 4 mm. Preferably, in one embodiment, the MRI image slice spacing $S_S$ is set for between approximately 1.8 mm and approximately 2.2 mm. More preferably, in one embodiment, the slice spacing $S_S$ is set for approximately 2 mm. For example, as can be understood from FIGS. 3 and 4, which are diagrammatic depictions of adjacent 2D MRI image slices 10a, 10b pertaining respectively to the knee joint or distal end 45a' of the femur 45a and the knee joint or proximal end 45b' of the tibia 45b, a 2 mm image slice spacing $S_S$ is the distance between immediately adjacent image slice 10a, 10b.

Figures 3, 5:
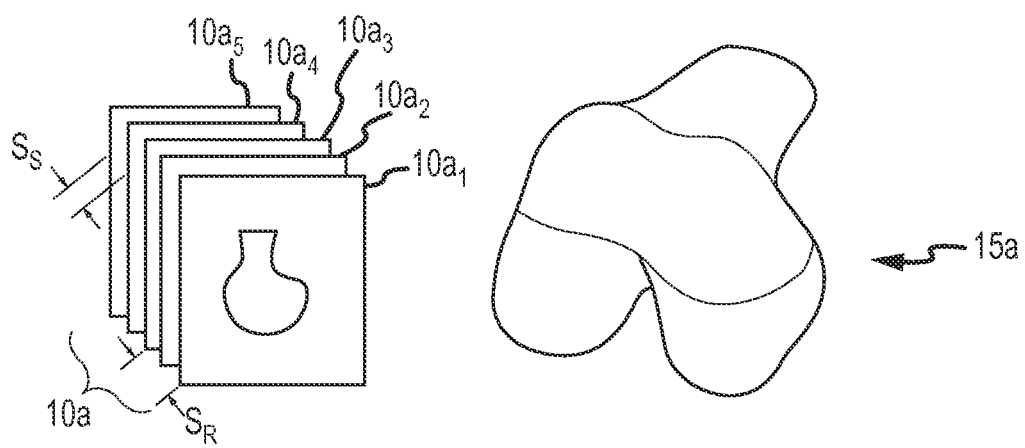
FIGS. 3 and 4 are diagrammatic depictions of adjacent 2D MRI image slices pertaining respectively to the knee joint or distal end of the femur and the knee joint or proximal end of the tibia.
FIGS. 5 and 6 are respective isometric views of computer generated distal femur end and proximal tibia end 3D bone models.
Figures 4, 6:
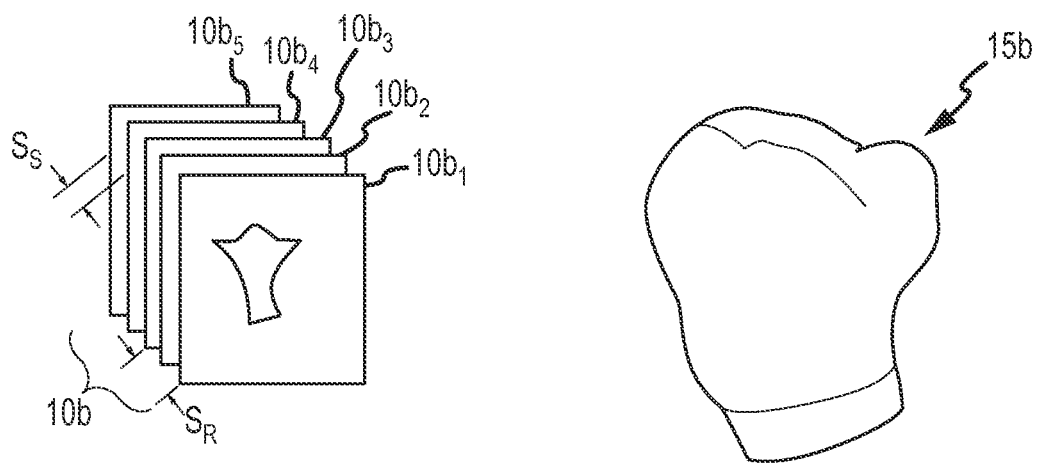

As can be understood from FIGS. 3 and 4, in one embodiment, the image slice spacing $S_S$ between immediately adjacent slices 10a, 10b is approximately 2 mm. However, because of signal to noise issues, in one embodiment, immediately adjacent MRI image slices 10a, 10b are not taken during the same run, but as discussed later in this Detailed Discussion, are taken via alternating scan runs. In other words, for example, a MRI image slice spacing $S_S$ of 2 mm "hardware" spacing may be obtained via a series of 4 mm image slice runs, as described later in this Detailed Description.

As described later in the Detailed Description with respect to FIGS. 3 and 4, a slice spacing $S_S$ of between approximately 1 mm and approximately 4 mm may be obtained via a series of two or more image scan runs. For example, to achieve a slice spacing $S_S$ of 1 mm, two image scan runs may be run with a scan run slice spacing $S_R$ of 2 mm. The two image scan runs, which are offset from each other in an alternating manner by 2 mm, are combined, resulting in image slices spaced apart from immediately adjacent image slices by a slice spacing $S_S$ of 1 mm.

In another example, to achieve a slice spacing $S_S$ of 1 mm, three image scan runs may be run with a scan run slice spacing $S_R$ of 3 mm. The three image scan runs, which are offset from each other in an alternating manner by 3 mm, are combined, resulting in image slices spaced apart from immediately adjacent image slices by a slice spacing $S_S$ of 1 mm.

Similar multiple scan runs and scan run slice spacings $S_R$ may be employed to obtain slice spacings $S_S$ of between approximately 1 mm and 4 mm. Of course, the greater the number of scan runs, the greater the time typically require to complete the scanning process.

While the aforementioned scan spacing $S_S$ ranges of approximately 1 mm to approximately 4 mm may be obtained via the running and combining of two or more scan runs having an appropriate scan run slice spacing $S_R$, the aforementioned scan spacing $S_S$ ranges of approximately 1 mm to approximately 4 mm may be obtained via a single scan run having a scan run spacing $S_R$ that is equal to the desired scan spacing $S_S$. In other words, each scan image is taken in succession during a single image scan run at the desired scan spacing $S_S$, which equals the scan run spacing $S_R$. Of course, typically, the smaller the scan run spacing $S_R$, the greater the likelihood of residual (i.e., noise) generation issues or the longer the time period necessary between the scanning of adjacent slice images.

Generally speaking, the signal to noise ratio is dependent upon the voxel size. As described above, in one embodiment, a pixel of a MRI scan is around 0.3 mm×0.3 mm×2 mm. The 2 mm slice thickness in the MRI set-up is not an absolute value. In other words, the slice thickness in MRI segmentation may be less or more than 2 mm.

Residuals are produced around the boundaries between each two adjacent scan slices 10a, 10b. Such residuals are called noise. If slice thickness or spacing for "hardware" spacing is quite big (e.g., 4 mm between each image slice), then residuals are reduced significantly as compared to small slice thickness or spacing for "hardware" spacing (e.g., 1 mm between each image slice). Accordingly, noise for large slice thickness or spacing is quite small between slices for a 4 mm slice thickness or spacing for "hardware" spacing. Unfortunately, large slice thickness or spacing can result in large errors for resulting water volume-averaging values. This is because each pixel is large compared to the pixels of small thickness or spacing slices, and the large pixels average water volume data over a larger volume and can produce higher errors. Therefore the "averaging" data of the volume produced in 4 mm thickness can produce higher errors.

On the other hand, for small thickness or spacing image slices such as 1 mm spacing for "hardware" spacing, although the water volume-averaging errors can be relatively small per pixel, the residuals produced around the smaller boundaries between each adjacent image slice will increase significantly. The small thickness or spacing image slices for "hardware" spacing result in a greater number of image slices with a greater potential for the generation of noise. Thus, MRI scans employing small spacing image slices for "hardware" spacing have the potential for greater accuracy. However, to take advantage of the increased accuracy, the time period overwhich the MRI takes place may need to be increased to allow sufficient time to run the large number image slices and to allow sufficient time between image slice scans for the residuals not to interfere with each other.

In one embodiment, to provide smaller slice spacing without the resulting increase in residuals, "hardware" image slice spacing may be modified via "software" image slice spacing to provide a smaller slice spacing. For example, MRI image slice spacing of 1 mm for "software" spacing can be generated from 2 mm MRI image slice spacing for "hardware" spacing without causing significant residuals or noise by using MRI software (e.g., as provided on General Electric MRI machines). Specifically, the MRI software takes the 2 mm "hardware" spacing image slices and interpolates the images to produce 1 mm "software" spacing image slices. Because it is based on the operation of software, "software" image spacing creates no noise occurs during the generation of 1 mm spaced image slices. This is in contrast to the generation of 1 mm spaced image slices via "hardware" spacing, wherein such narrow spacing may cause significant noise. The 1 mm "software" spacing process does not require a substantial processing time, as compared to 2 mm image slice spacing generated via "hardware" spacing.

Thus, as can be understood from the immediately preceding discussion, "hardware" spacing pertains to MRI images directly obtained from the machine. For example, the MRI machine may be set for a 2 mm image slice spacing and then simply produce image slices so spaced without any other procedures. In other words, "hardware" spacing may be the result of the standard MRI machine settings and operations and not additional software processes. In contrast, "software" spacing is spacing based on "hardware" spacing, which is modified, adapted or interpolated via software to obtain a different image spacing. For example, a 2 mm "hardware" image spacing is generated by the MRI machine and "software" image spacing employs software that uses image slices from the 2 mm hardware image spacing to provide additional image slices by interpolating the 2 mm space images. As a result, image slices at a 2 mm "hardware" image spacing may be interpolated to provide image slices at a 1 mm "software" image spacing.

In one embodiment, for MRI to be feasible for the generation of 2D images 10 that are used to create computer generated 3D bone models 15, the MRI must be configured such that a MRI procedure is sufficiently quick that the vast majority of patients can hold completely still for the entire procedure and the MRI slice images have adequate resolution. Achieving these goals is, in part, a function of selecting a proper balance between MRI pixel size, resolution, slice thickness and order in which to make each slice.

As can be understood from FIGS. 3 and 4, in one example embodiment, each slice 10a, 10b is spaced apart from its immediately adjacent slice 10a, 10b by an image slice spacing $S_S$ for "hardware" spacing of approximately 2 mm. For example, femur image slices $10a_1$, $10a_2$, $10a_3$, $10a_4$, and $10a_5$ may be at, respectively, 1 mm, 3 mm, 5 mm, 7 mm and 9 mm, and tibia image slices $10b_1$, $10b_2$, $10b_3$, $10b_4$, and $10b_5$ may be at, respectively, 1 mm, 3 mm, 5 mm, 7 mm and 9 mm.

In some embodiments, a 2 mm image slice spacing $S_S$ may be quite close with respect to the generation of residuals. Accordingly, in one embodiment, the MRI imager 40 runs a first set of image slices $10a_1$, $10a_3$ and $10a_5$ for the femur images 10a and a first set of image slices $10b_1$, $10b_3$ and $10b_5$ for the tibia images 10b. In other words, the MRI imager 40 skips performing the even numbered images $10a_2$, $10a_4$, $10b_2$, $10b_4$ and performs only the odd numbered images $10a_1$, $10a_3$, $10a5$, $10b_1$, $10b_3$ and $10b_5$ in the first run. Thus, the first set of femur image slices $10a_1$, $10a_3$ and $10a_5$ and a first set of tibia image slices $10b_1$, $10b_3$ and $10b_5$ will be, respectively, 1 mm, 5 mm and 9 mm. The resulting run slice spacing $S_R$ for the first set of femur and tibia images is 4 mm, which is sufficiently large to avoid generating significant noise from residuals.

Once the residuals from the first set or run has subsided, the MRI imager 40 runs a second set of image slices $10a_2$ and $10a_4$ for the femur images 10a and a second set of image slices $10b_2$ and $10b_4$ for the tibia images 10b. In other words, the MRI imager 40 skips performing the odd numbered images $10a_1$, $10a_3$, $10a_5$, $10b_1$, $10b_3$, $10b_5$ and performs only the even numbered images $10a_2$, $10a_4$, $10b_2$, $10b_4$ in the second run. Thus, the second set of femur image slices $10a_2$ and $10a_4$ and a second set of tibia image slices $10b_2$ and $10b_4$ will be, respectively, 3 mm and 7 mm. The resulting run slice spacing $S_R$ for the second set of femur and tibia images is 4 mm, which is sufficiently large to avoid generating significant noise from residuals.

As can be understood from FIGS. 3 and 4, in another example embodiment, each slice 10a, 10b is spaced apart from its immediately adjacent slice 10a, 10b by an image slice spacing $S_S$ for "hardware" spacing of approximately 2 mm. For example, femur image slices $10a_1$, $10a_2$, $10a_3$, $10a_4$, and $10a_5$ may be at, respectively, 2 mm, 4 mm, 6 mm, 8 mm and 10 mm, and tibia image slices $10b_1$, $10b_2$, $10b_3$, $10b_4$, and $10b_5$ may be at, respectively, 2 mm, 4 mm, 6 mm, 8 mm and 10 mm.

In some embodiments, a 2 mm image slice spacing $S_S$ may be quite close with respect to the generation of residuals. Accordingly, in one embodiment, the MRI imager 40 runs a first set of image slices $10a_1$, $10a_3$ and $10a_5$ for the femur images 10a and a first set of image slices $10b_1$, $10b_3$ and $10b_5$ for the tibia images 10b. In other words, the MRI imager 40 skips performing the even numbered images $10a_2$, $10a_4$, $10b_2$, $10b_4$ and performs only the odd numbered images $10a_1$, $10a_3$, $10a5$, $10b_1$, $10b_3$ and $10b_5$ in the first run. Thus, the first set of femur image slices $10a_1$, $10a_3$ and $10a_5$ and a first set of tibia image slices $10b_1$, $10b_3$ and $10b_5$ will be, respectively, 2 mm, 6 mm and 10 mm. The resulting run slice spacing $S_R$ for the first set of femur and tibia images is 4 mm, which is sufficiently large to avoid generating significant noise from residuals.

Once the residuals from the first set or run has subsided, the MRI imager 40 runs a second set of image slices $10a_2$ and $10a_4$ for the femur images 10a and a second set of image slices $10b_2$ and $10b_4$ for the tibia images 10b. In other words; the MRI imager 40 skips performing the odd numbered images $10a_1$, $10a_3$, $10a_5$, $10b_1$, $10b_3$, $10b_5$ and performs only the even numbered images $10a_2$, $10a_4$, $10b_2$, $10b_4$ in the second run. Thus, the second set of femur image slices $10a_2$ and $10a_4$ and a second set of tibia image slices $10b_2$ and $10b_4$ will be, respectively, 4 mm and 8 mm. The resulting run slice spacing $S_R$ for the second set of femur and tibia images is 4 mm, which is sufficiently large to avoid generating significant noise from residuals.

For either of the image run examples discussed immediately above with respect to FIGS. 3 and 4, making two sets of 4 mm offset image runs (i.e., a set of odd images and a set of even images having image run spacings $S_R$ of approximately 4 mm) and combining the two run sets together results in a series of femur image slices $10a_1$, $10a_2$, $10a_3$, $10a_4$, and $10a_5$ a series of tibia image slices $10b_1$, $10b_2$, $10b_3$, $10b_4$, and $10b_5$ that have an actual image slice spacing $S_S$ for "hardware" spacing of approximately 2 mm between immediately adjacent image slices 10a, 10b.

As stated above, running 2 mm actual image slice spacing $S_S$ for "hardware" spacing without alternating between odd image runs and even image runs may, in some embodiments, result in interference and noise between the immediately adjacent image slices 10a, 10b. An actual image slice spacing $S_S$ for "hardware" spacing of approximately 2 mm achieved via combining first and second alternating image runs having run image spacings $S_R$ for "hardware" spacing of approximately 4 mm, coupled with a 256×256 resolution, can reduce MRI imaging time from 30 to 45 minutes or more to approximately 3 minutes or less, while still providing image resolution sufficient for generating 3D bone models 15 from the 2D MRI image slices 10.

While the aforementioned examples are given in the context of achieving a 2 mm slice spacing $S_S$ via combining two scan runs having a 4 mm scan run spacing $S_R$ and at a resolution of 256×256, it should be noted that other scan run spacings $S_S$ of between approximately 1 mm and 4 mm may be obtained via a single scan run or the combining of multiple scan runs and at a variety of resolutions of between approximately 128×128 and approximately 1024×1024. Consequently, the system and method disclosed herein should not be limited to a specific slice spacing $S_S$ or resolution, except as specifically stated in the claims. The time needed to achieve a MRI image scanning process will depend, at least in part, on the slice spacing $S_S$ selected, and whether or not the time is too long for a specific patient will depend on the condition and characteristics of the patient.

As can be understood from FIG. 1, the orientation of the MRI image slicing is calibrated or adjusted to result in 2D MRI image slices 10 that are readily useable by 3D computer modeling programs to generate 3D bone models 15 [block 1020]. Further discussion regarding the orientation process is provided later in this Detailed Description.

As indicated in FIGS. 1 and 2, 2D MRI image slices 10 of the patient's knee joint 35 are generated via the MRI imager 40 [block 1030]. While the preceding and following discussions are made in the context of knee joints, femurs and tibias, the systems and methods disclosed in this Detailed Description are equally applicable to other joints (e.g., hips, shoulders, elbows, wrists, ankles, spinal vertebra intersections, etc.) and the manufacture of customized arthroplasty jigs for arthroplasty procedures involving such diverse types of joints. Accordingly, the systems and methods disclosed in this Detailed Description should not be considered to be limited to knees or customized femur and tibia arthroplasty jigs, but should be considered as encompassing all types of joints and customized arthroplasty jigs for all types of joints.

The generated 2D MRI slices 10 are provided to a CPU 50 that employs 3D modeling computer software to create various 3D bone models and/or 3D bone and cartilage models 15 [block 1040], similar to those depicted in FIGS. 5 and 6, which are respective isometric views of computer generated distal femur end and proximal tibia end 3D bone models 15a, 15b. The CPU 50 is then used to analyze and manipulate the 3D bone images 15 to generate data pertaining to customized arthroplasty jigs 20 [block 1050]. The generated data may include bone surface information and saw cut and/or drill hole information. The bone surface information pertains to surfaces of the femur and/or tibia bones 45a, 45b that will mate with the customized arthroplasty jigs 20 and/or that may be the target of the arthroplasty procedure. The saw cut and drill hole information may pertain respectively to saw cuts and drill holes to be made in the femur and/or tibia bones 45a, 45b during the arthroplasty procedure.

For a discussion of (1) candidate 3D computer modeling software programs, (2) methods of generating 3D bone models from 2D MRI image slices 10, (3) bone surface information, (4) saw cut and drill hole information, and (5) methods of employing such 3D models and information to produce customized arthroplasty jigs, see U.S. patent application Ser. No. 11/656,323, which is entitled "Arthroplasty Devices And Related Methods" and was filed by Park et al. on Jan. 19, 2007. For a discussion of customized arthroplasty jigs that may be produced via the methods disclosed in the Detailed Description and U.S. patent application Ser. No. 11/656,323, see U.S. patent application Ser. No. 11/642,385, which is entitled "Arthroplasty Devices And Related Methods" and was filed by Park et al. on Dec. 19, 2006. The disclosures of U.S. patent application Ser. Nos. 11/656,323 and 11/642,385 are incorporated by reference into this Detailed Description in their entireties.

As can be understood from FIGS. 1 and 2, the data is provided from the CPU 50 to the manufacturing device(s) 55, which may be a CNC milling machine or other type of machining or forming machine. The manufacturing device(s) 55 employ the bone surface information to create surfaces 57 on a jig blank 60 that are configured to matingly receive the surfaces of the bone 45 that are the target of the arthroplasty procedure [block 1070]. The jig blank 60 may be a near-shape arthroplasty jig blank 60 similar to those discussed in U.S. patent application Ser. No. 11/656,323, where the jig blank is sized or selected to be near the size of the resulting jig 20 to reduce the amount of jig blank material that needs to be machined away, thereby reducing machining time, costs and waste.

Figure 7:
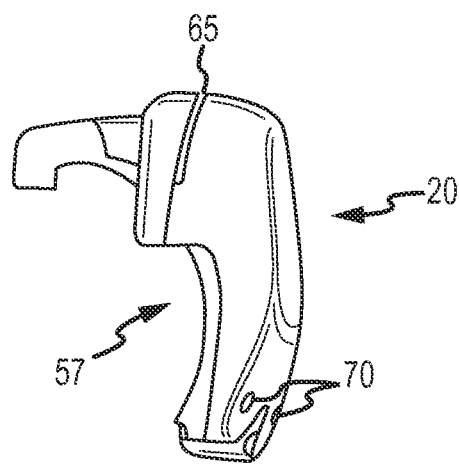
FIG. 7 is a side view of a femur arthroplasty jig.

The manufacturing device(s) 55 employ the saw cut and drill hole information to create saw cut slots 65 and drill holes 70 in the jig blank 60 [block 1080]. The result of using the bone surface information and saw cut and drill hole information to machine or otherwise form the jig blank 60 is a customized arthroplasty jig 20, as depicted in FIG. 7, which is a side view of a femur arthroplasty jig 20. The resulting jig 20 has surfaces 57 for matingly receiving target bone surfaces. The resulting jig 20 also has saw cut slots 65 and drill holes 70 that respectively guide a bone saw in making cuts in the surfaces of the target bone 45 and drill bits in making drill holes in the surfaces of the target bone 45 when the jig 20 is matingly receiving the target bone surface during the arthroplasty procedure.

Figure 8:
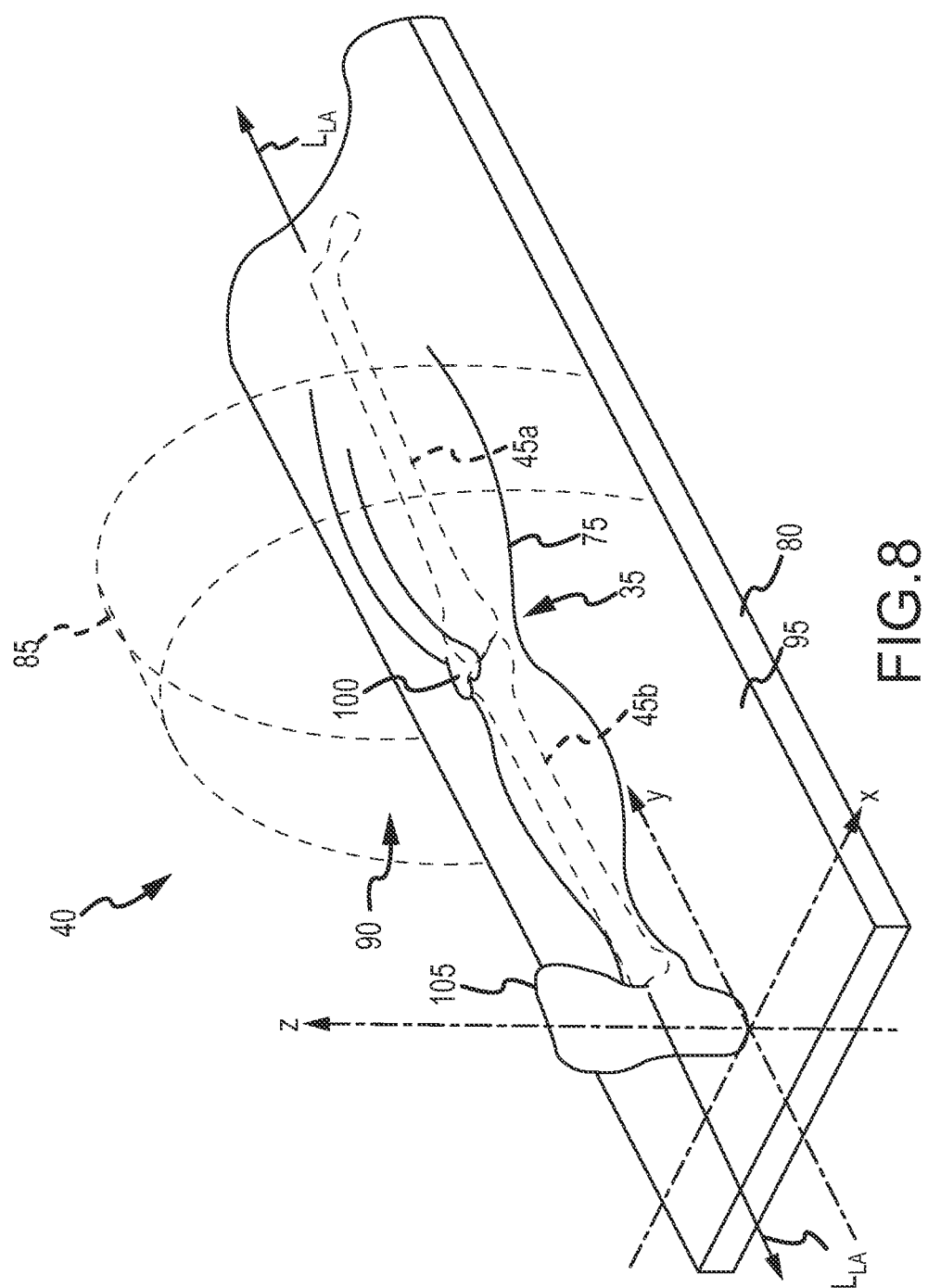
FIG. 8 is an isometric view of a patient's joint located in a MRI imager.

For a discussion of the system and method for orienting the MRI image slicing ([block 1020] of FIG. 1) and the system and method for generating MRI image slices ([block 1030] of FIG. 1), reference is made to FIG. 8, which is an isometric view of a patient's joint 35 located in a MRI imager 40. As shown in FIG. 8, a patient's leg 75 is positioned on a platform 80 of the MRI imager 40 such that the patient's knee joint 35 is located within the scanning area 85 of the MRI imager 40. The scanning area 85 may be that of a dedicated extremity coil (e.g., a knee coil in the context of a knee being scanned, an elbow coil in the context of an elbow being scanned, etc.), which may include an opening 90 through which the leg 75 extends.

The platform 80 may be used for supporting the patient or a portion of a patient being imaged via the MRI imager 40. The platform 80 may be used to move the patient or portion of the patient into the opening 90 of the scanning area 85. The platform 80 may be used to orient the patient's leg 75 such that the longitudinal axis $L_{LA}$ of the leg is generally parallel to axis Y of the MRI imager 40.

As can be understood from FIG. 8, axis Y of the MRI imager 40 may be generally parallel to a longitudinal axis of the platform 80. However, in more general terms, axis Y may be oriented such that it extends though the scanning area 85 generally normal to the opening 90 of the scanning area 85. Axis X of the MRI imager 40 extends generally perpendicular to axis Y in the same plane as axis Y (i.e., axis Y and axis X define plane X-Y). Plane X-Y may be generally parallel to the platform top surface 95 on which the leg 75 is resting.

Axis Z of the MRI imager 40 extends generally perpendicular to axis Y in the same plane as axis Y (i.e., axis Y and axis Z define plane Y-Z). Axis Z also extends generally perpendicular to axis X in the same plane as axis X (i.e., axis X and axis Z define plane X-Z).

As can be understood from FIG. 8, in one embodiment, to facilitate proper MRI image slicing that is useable with the above-described MRI image resolutions and image slice spacings to readily and reliably create computer generated 3D bone models 15, the leg 75 may be oriented in the MRI imager 40 such that the longitudinal axis $L_{LA}$ of the leg 40 is generally parallel to axis Y and generally perpendicularly transverse to axis X. Furthermore, the leg 75 is rotationally oriented about the leg longitudinal axis $L_{LA}$ such that the patient's patella 100 and toes 105 extend generally parallel to axis Z or, in other words, generally perpendicular to plane X-Y. Thus, as can be understood from FIG. 9, which is the same view depicted in FIG. 8, except only the femur 45a and tibia 45b of the patient's leg 75 are shown, the anterior and posterior sides of the femur 45a and tibia 45b face in directions that are generally parallel to axis Z or, in other words, generally perpendicular to plane X-Y. Also, the medial and lateral sides of the femur 45a and tibia 45b face in directions that are generally parallel to axis X or, in other words, generally perpendicular to plane Y-Z. In other words, the coronal view of the femur 45a and tibia 45b faces in a direction that is generally parallel to axis Z or, in other words, generally perpendicular to plane X-Y. Also, sagittal views of the femur 45a and tibia 45b face in directions that are generally parallel to axis X or, in other words, generally perpendicular to plane Y-Z.

Figure 9:
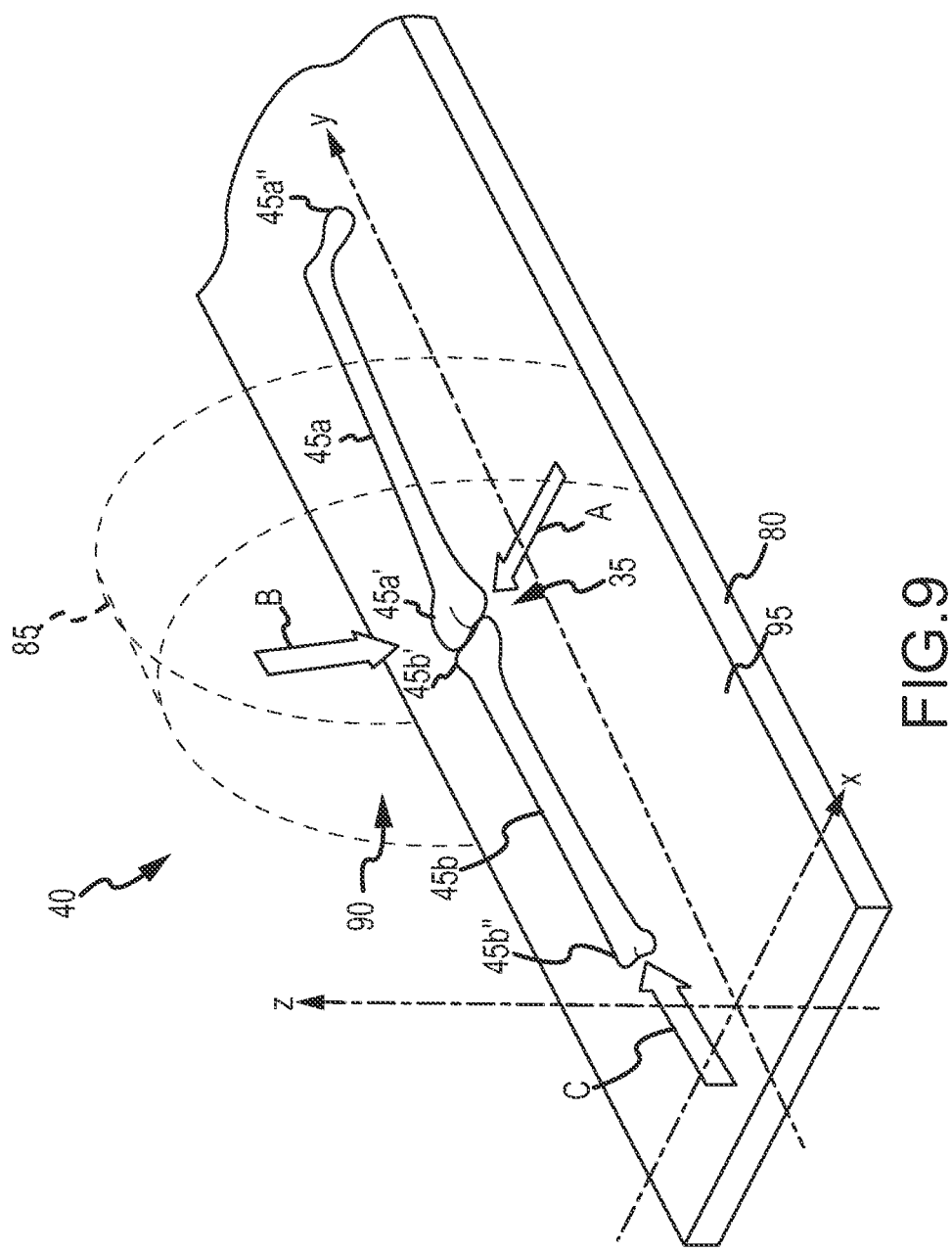
FIG. 9 is the same view depicted in FIG. 8, except only the femur and tibia of the patient's leg are shown.

In one embodiment, orienting the femur 45a and tibia 45b as indicated in and discussed with respect to FIGS. 8 and 9 results in the generation of properly oriented sagittal MRI image slices of the femur 45a and tibia 45b. As can be understood from FIGS. 8 and 9, where the femur 45a and tibia 45b are properly oriented as indicated in and discussed with respect to FIGS. 8 and 9, in one embodiment, a properly oriented sagittal MRI image slice is a plane parallel to the Y-Z plane indicated in FIGS. 8 and 9. In other words, in one embodiment, a properly oriented sagittal MRI image slice is a plane through the femur and tibia that is: (1) generally perpendicular to a joint line of the knee or generally perpendicular to the ground when the patient is standing upright on the leg; and (2) generally parallel to planes that are tangential to the medial and lateral sides of the femur condyles. In one embodiment, a properly oriented sagittal MRI image slice is a plane that is parallel to a plane that bilaterally divides the femur and tibia into generally symmetrical medial and lateral portions. Where the femur and tibia are properly oriented on the platform 80 as depicted in FIGS. 8 and 9, a properly oriented sagittal MRI image slice would be in a plane through the femur and tibia generally perpendicular to the view arrow A in FIG. 9, which points in a direction generally perpendicular to plane Y-Z.

Figure 10:
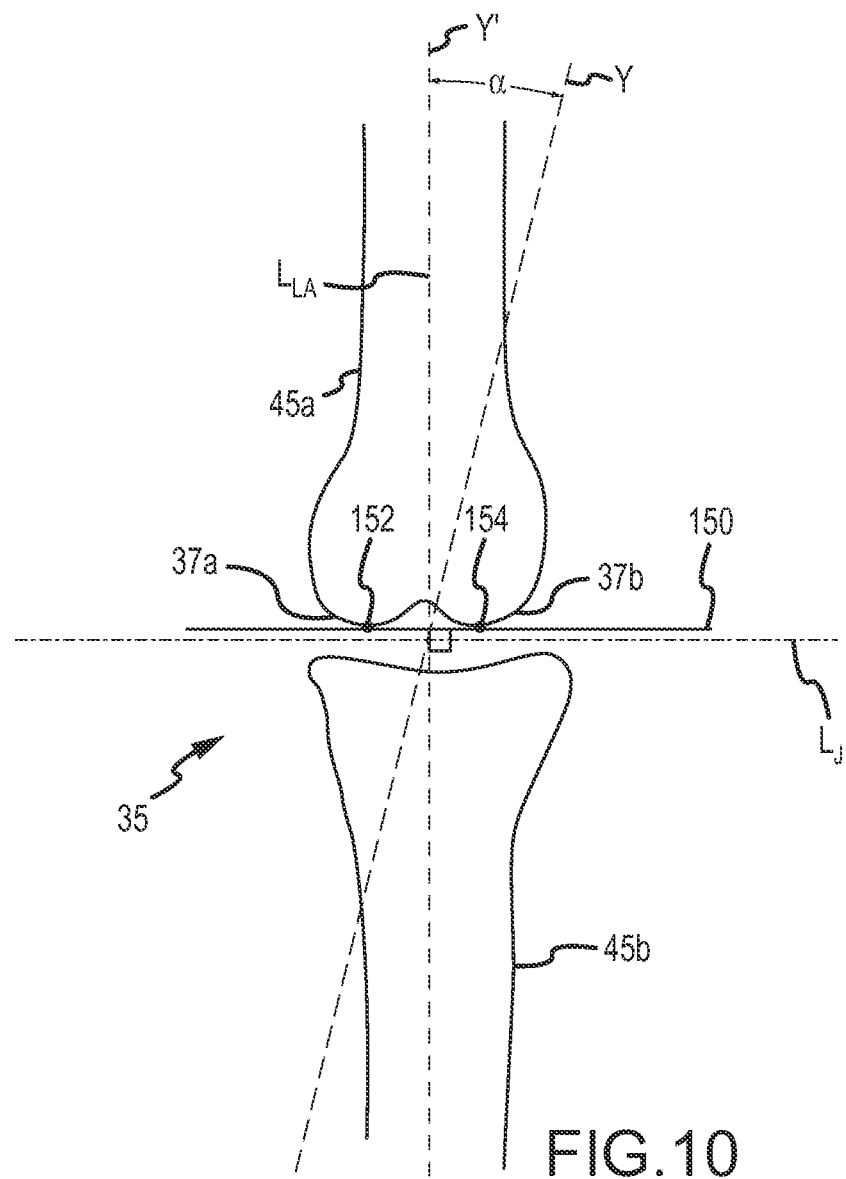
FIG. 10 is an anterior-posterior or coronal view of the femur and tibia as viewed from the direction of arrow B in FIG. 9.
Figure 11:
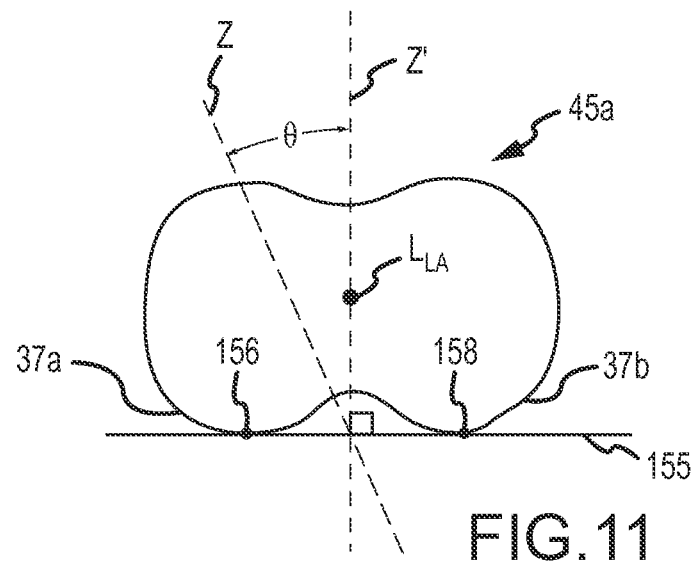
FIG. 11 is an axial view of the femur as viewed from the direction of arrow C in FIG. 9 and wherein the knee is 90 degree flexion.
Figure 12A:
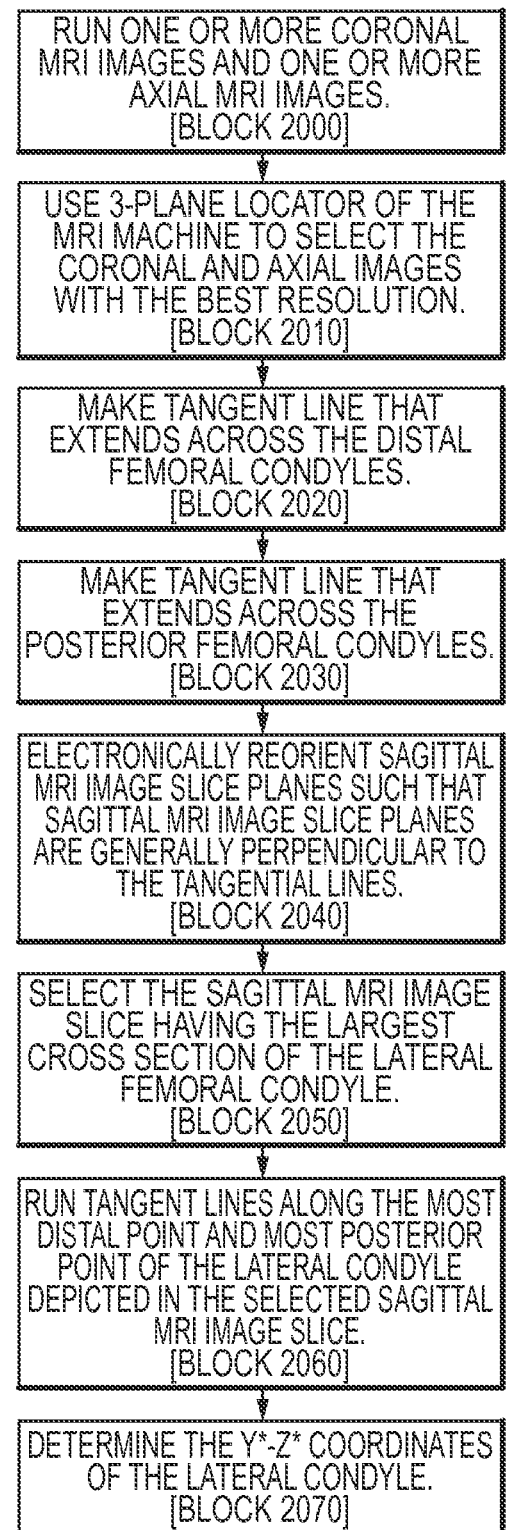
FIGS. 12A-12C contain a flow chart depicting the method of orienting the MRI image slicing and method of generating MRI image slices referenced in FIG. 1.
Figure 12B:
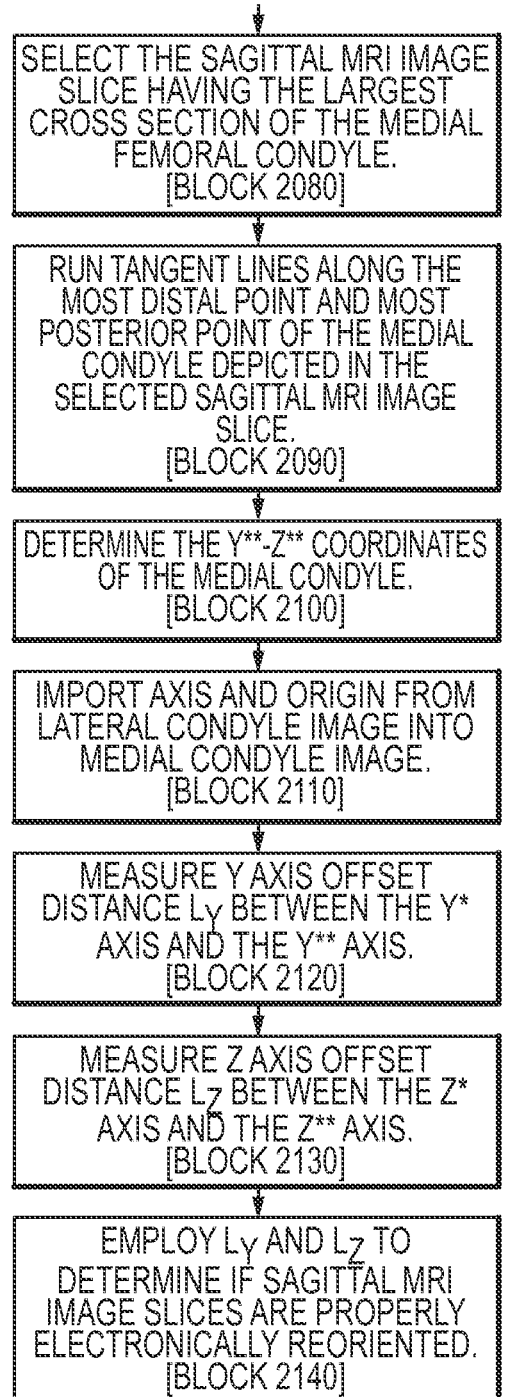
Figure 12C:
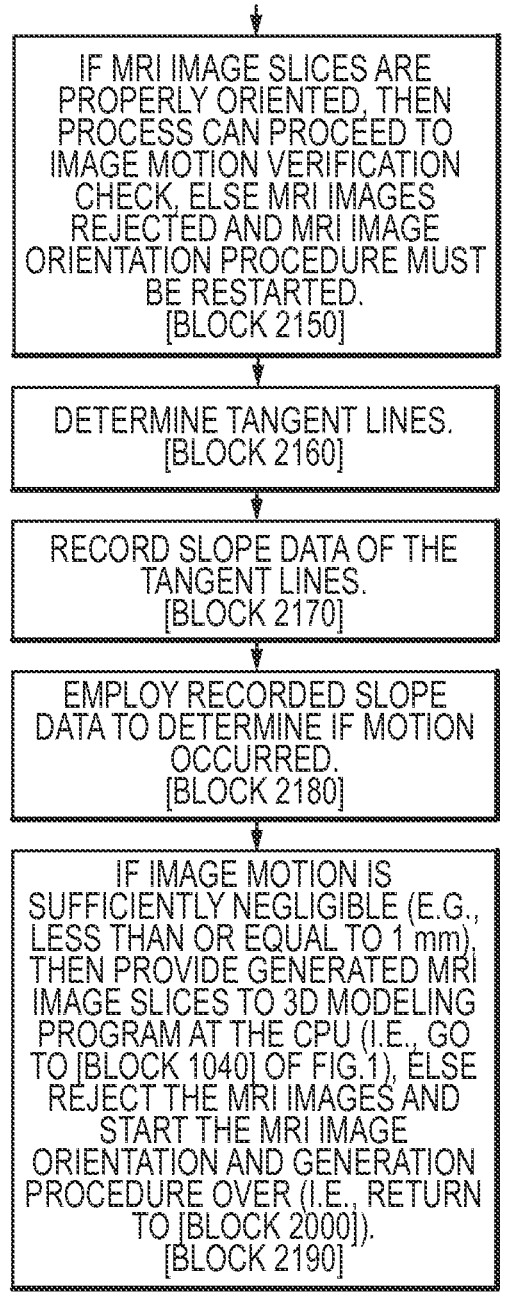

For at least the following reasons, the femur 45a and tibia 45b may not be physically oriented on the platform 80, as discussed above with respect to FIGS. 8 and 9, to achieve properly oriented sagittal MRI image slices. In other words, for at least the following reasons, it may be difficult, if not impossible, to properly physically orient the femur and tibia on the platform 80 to obtain properly oriented sagittal MRI image slices. For instance, the operator of the MRI imager 40 may not take the time to properly physically orient the patient's leg 75 to achieve the above-discussed femur and tibia orientation within the MRI imager 40. Furthermore, even with the operator's best efforts, the above-discussed femur and tibia orientation may not be achieved due to unusual bone structure not apparent from the overall shape of the leg 75, the size and configuration of the patient and/or machine preventing the operator from properly orienting the patient in the MRI imager 40, and/or the femur 45a and tibia 45b do not both substantially extend along the same longitudinal axis (e.g., due to injury or degenerative disease, the longitudinal axis of the tibia and the longitudinal axis of the femur substantially deviate from each other at the knee).

Where the femur 45a and tibia 45b are not properly physically oriented on the platform 80 as depicted in FIGS. 8 and 9, the femur 45a and tibia 45b may be improperly or randomly physically oriented on the platform 80 as depicted in FIGS. 10 and 11. FIG. 10 is an anterior-posterior or coronal view of the femur and tibia as viewed from the direction of arrow B in FIG. 9, wherein arrow B points in a direction perpendicular to plane X-Y. FIG. 11 is an axial view of the femur as viewed from the direction of arrow C in FIG. 9, wherein the knee is in 90 degree flexion and arrow C points in a direction perpendicular to plane X-Z.

As can be understood from FIG. 10, a line 150 can be drawn to intersect two extreme distal points 152, 154 on the femur condyles 37. The distal condyle intersecting line 150 is generally parallel to the joint line $L_J$ of the knee joint 35. The longitudinal axis $L_{LA}$ of the femur 45a and tibia 45b may be be aligned with or extend along axis Y', which is generally perpendicular to the intersecting line 150 and offset by an angle α from axis Y of the platform 80 in FIG. 9. Thus, if the femur and tibia are improperly or randomly physically oriented on the platform 80 in a manner similar to that depicted in FIG. 10, the femur and tibia will be, for the purposes of achieving proper sagittal MRI image slices, transversely out of alignment with plane Y-Z by an angle α. In other words, without electronically reorienting the femur and tibia, as described later in this Detailed Description, the MRI machine 40 will form its sagittal MRI image scans under the mistaken assumption that the femur and tibia are properly physically aligned along axis Y as depicted in FIGS. 8 and 9.

As can be understood from FIG. 11, a line 155 can be drawn to intersect two extreme posterior points 156, 158 on the posterior surfaces of the femur condyles 37. The posterior condyle intersecting line 155 is generally perpendicular to axis Z', which is offset by an angle θ from axis Z of the platform 80 in FIG. 9. Thus, if the femur and tibia are improperly or randomly physically oriented on the platform 80 in the manner similar to that depicted in FIG. 11, the femur and tibia will be, for the purposes of achieving proper sagittal MRI image slices, rotationally out of alignment with plane Y-Z by an angle θ. In other words, without electronically reorienting the femur and tibia, as described later in this Detailed Description, the MRI machine 40 will form its sagittal MRI image scans under the mistaken assumption that the femur and tibia are properly physically rotationally oriented with respect to plane Y-Z as depicted in FIGS. 8 and 9.

Where, as depicted in FIGS. 10 and 11, the femur and tibia are not properly physically oriented on the platform 80 to achieve properly oriented sagittal MRI image slices, the resulting sagittal MRI image slices are likely to be unacceptable for the purposes of making computer generated 3D bone models. Absent the following system and method for electronically correcting the orientation of the femur and tibia when the femur 45a and tibia 45b are improperly or randomly physically positioned on the platform 80 (proper femur and tibia physical orientation on the platform being depicted in FIGS. 8 and 9), the resulting MRI process would have to be repeated. This repeating of the MRI process wastes patient and medical staff time, increasing the emotional and monetary cost of the procedure.

Figure 13:
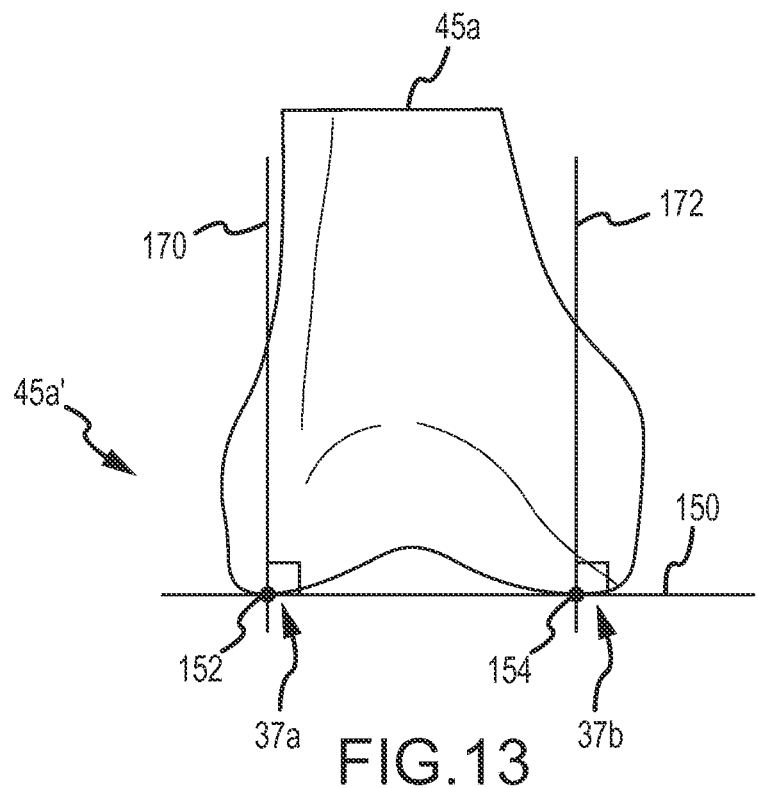
FIGS. 13 and 14 are, respectively, coronal and axial views of a distal or joint end of a femur, wherein condyle intersecting lines are determined.
Figure 14:
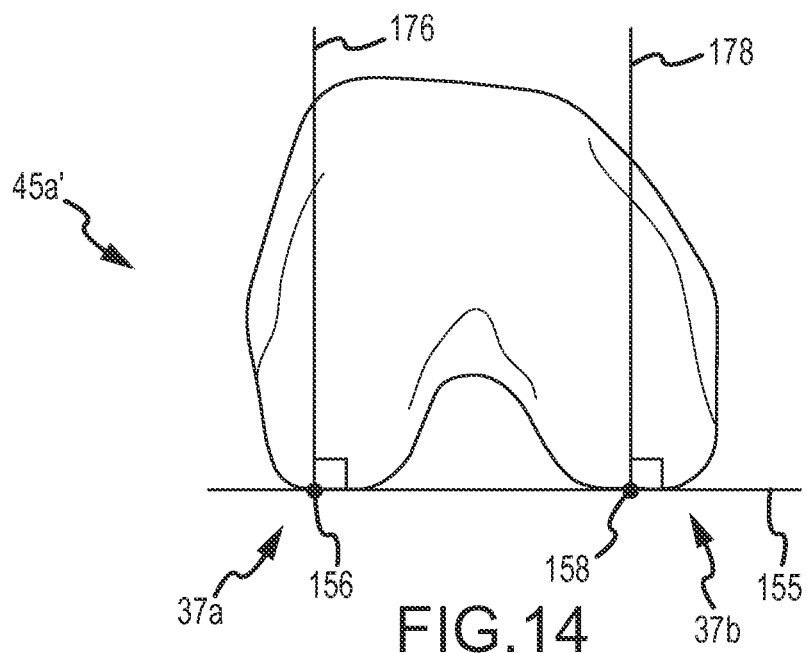

For a detailed discussion of the method of orienting the MRI image slicing ([block 1020] indicated in FIG. 1) and the method of generating MRI image slices ([block 1030] indicated in FIG. 1), reference is first made to FIGS. 12-16. FIGS. 12A-12C contain a flow chart depicting the method of orienting and generating MRI image slicing [blocks 1020 & 1030] referenced in FIG. 1. FIGS. 13 and 14 are, respectively, coronal and axial views of a distal or joint end 45a' of a femur 45, wherein condyle intersecting lines 150, 155 are determined. FIGS. 15 and 16 are, respectively, coronal and axial MRI image views illustrating the application of the condyle intersecting lines 150, 155 to electronically orient the sagittal MRI image slice planes 160. In one embodiment, the following discussion regarding FIGS. 12-16 and subsequent figures describes a method of electronically reorienting the femur and tibia when the femur and tibia are not physically properly oriented on the MRI platform 80.

As shown in FIG. 13, point 152 represents a tangent contact point at the lowest or most distal extremity of the lateral femoral condyle 37a obtained in the $m^{th}$ slice, where m equals integers 1, 2, 3, . . . 50. Point 154 represents a tangent contact point at the lowest or most distal extremity of the medial femoral condyle 37b obtained in the $n^{th}$ slice, where n equals integers 1, 2, 3, . . . 50, except the m integer. Line 150 extends across the distal ends of the condyles 37 to intersect both tangent contact points 152, 154. In this normal femur model 45a depicted in FIG. 13, line 150 is parallel or nearly parallel to the joint line $L_J$ of the knee joint 35, as depicted in FIG. 10.

As shown in FIG. 13, reference lines 170, 172 respectively extend from points 152, 154 generally perpendicularly to line 150. As will be understood from the discussion regarding FIG. 15, these reference lines 170, 172 are generally parallel to properly oriented sagittal MRI image slices.

As shown in FIG. 14, point 156 represents a tangent contact point at the most posterior extremity of the lateral femoral condyle 37a obtained in the $q^{th}$ slice, where q equals integers 1, 2, 3, . . . 50. Point 158 represents a tangent contact point at the most posterior extremity of the medial femoral condyle 37b obtained in the $r^{th}$ slice, where r equals integers 1, 2, 3, . . . 50, except the q integer. Line 155 extends across the distal ends of the condyles 37 to intersect both tangent contact points 156, 158.

As shown in FIG. 14, reference lines 176, 178 respectively extend from points 156, 158 generally perpendicularly to line 155. As will be understood from the discussion regarding FIG. 16, these reference lines 176, 178 are generally parallel to properly oriented sagittal MRI image slices.

As can be understood from FIGS. 1, 15 and 16, once the patient's leg 75 is positioned in the scanning area 85 of the MRI machine 40, in one embodiment, the MRI technician runs one or more coronal MRI images (see FIG. 15) and/or one or more axial MRI images (see FIG. 16) [block 2000]. The MRI technician uses the 3-plane locator of the MRI machine 40 to select the coronal and axial images with the best resolution [block 2000]. The localizer line 150 is adjusted in the coronal MRI image (FIG. 15) to tangentially intersect the cortical-cancellous bone edge 38 of the most distal extremities of the femur condyles 37 in the same manner discussed with respect to FIG. 13, thereby making a tangent line 150 that extends across the distal femoral condyles [block 2020]. Additionally or alternatively, the localizer line 155 is adjusted in the axial MRI image (FIG. 16) to tangentially intersect the cortical-cancellous bone edge 38 of the most posterior extremities of the femur condyles 37 in the same manner discussed with respect to FIG. 14, thereby making a tangent line 155 that extends across the posterior femoral condyles [block 2030]. The sagittal MRI image slice planes 160 are then electronically reoriented such that sagittal MRI image slice planes 160 are generally perpendicular to one or both of the tangential localizer lines 150, 155 [block 2040]. By electronically reorienting the sagittal MRI image slice planes 160 to be perpendicular to one or both of the localizer lines 150, 155, the resulting sagittal MRI image slices appear as if the leg was properly physically oriented in the MRI machine 40 like depicted in FIGS. 8 and 9 although, in actuality, the leg was really improperly physically oriented in the MRI machine as depicted in FIGS. 10 and 11. Accordingly, regardless of the actual orientation of the leg within the MRI machine, the resulting MRI image slices will be readily and reliably usable to create computer generated 3D bone images.

As previously discussed in this Detailed Discussion, in one embodiment, the MRI image slice planes 160 may be 4 mm apart, and two staggered imaging runs or sets (e.g., running odd number slices and then even numbered slices) are combined to obtain a slice spacing wherein immediately adjacent slices are 2 mm apart.

Figure 17:
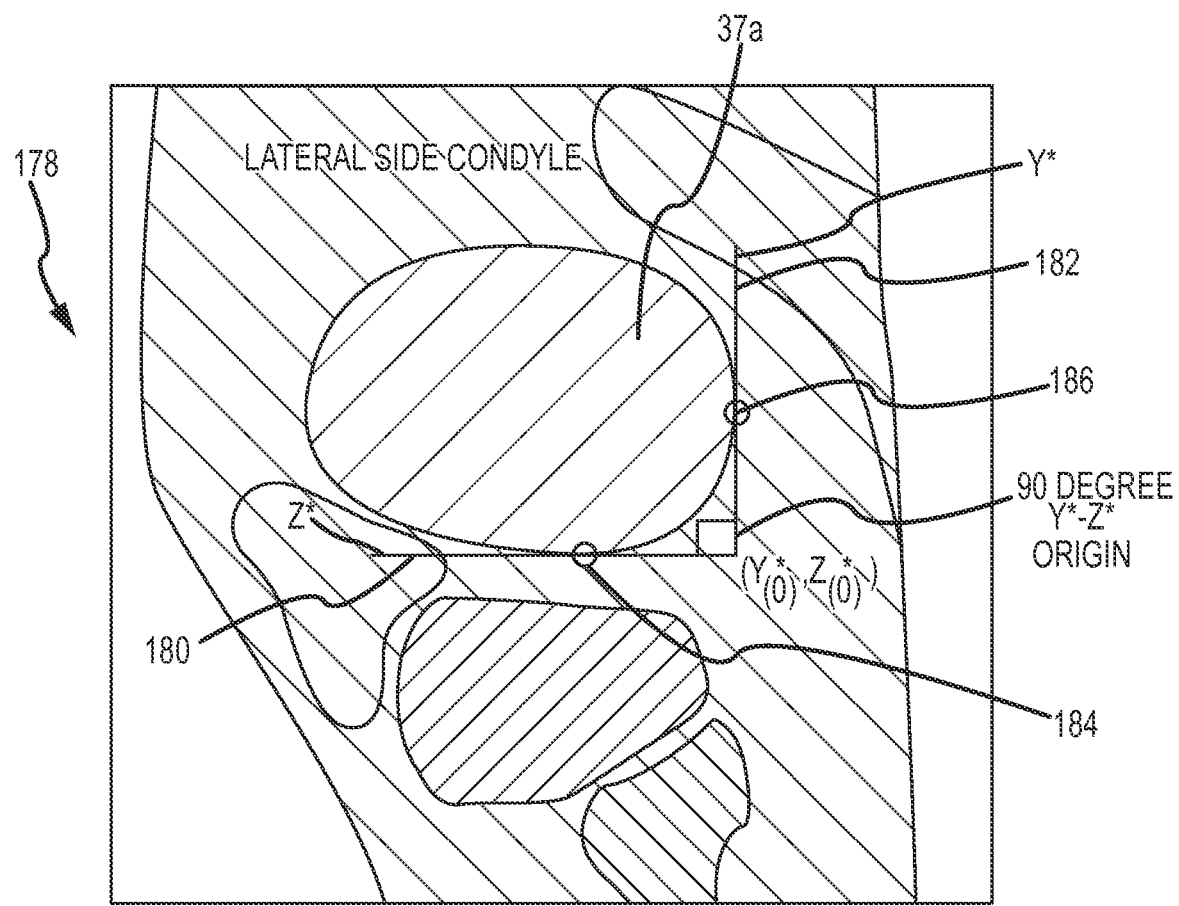
FIG. 17 is a sagittal MRI image slice of the lateral femur condyle taken in the vicinity of point in FIG. 13.
Figure 18:
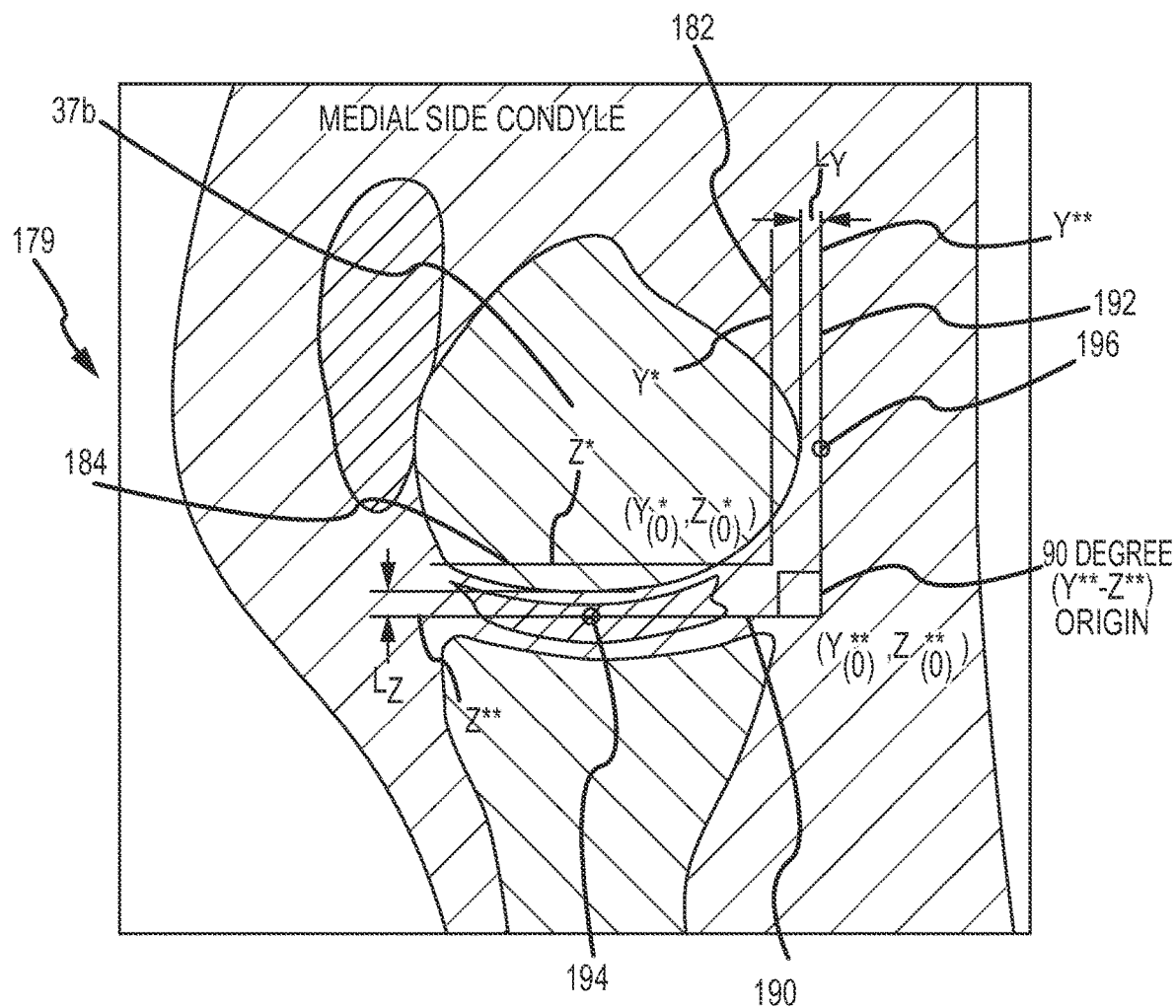
FIG. 18 is a sagittal MRI image slice of the medial femur condyle taken in the vicinity of point in FIG. 13.

To verify the slice planes 160 are properly electronically oriented, a verification process is run. For a discussion of the verification process, reference is made to FIGS. 12A-12C, 17 and 18. FIG. 17 is a sagittal MRI image slice 178 of the lateral femur condyle 37a taken in the vicinity of point 152 in FIG. 13. FIG. 18 is a sagittal MRI image slice 179 of the medial femur condyle 37b taken in the vicinity of point 154 in FIG. 13.

Depending on the embodiment, the verification process can be performed either manually or automatically. From the series of sagittal MRI images slices generated via the MRI machine 40, the sagittal MRI image slice 178 having the largest cross section of the lateral femoral condyle 37a is selected [block 2050]. Tangent lines 180, 182 are run along the most distal point 184 and most posterior point 186 of the lateral condyle 37a depicted in the selected sagittal MRI image slice 178 [block 2060]. The points 184, 186 serve as the landmark reference points for the lateral image 178. The two tangent lines 182, 180 are each parallel to the electronically reoriented Y-Z plane and respectively form axis Y* and axis Z*. The two tangent lines 180, 182 are generally perpendicular to each other, as indicated in FIG. 17, and intersect at the Y*-Z* origin, which is set as $(Y^*_0, Z^*_0)$. Therefore, the Y*-Z* coordinates of the lateral condyle 37a are obtained and determined [block 2070].

From the series of sagittal MRI images slices generated via the MRI machine 40, the sagittal MRI image slice 179 having the largest cross section of the medial femoral condyle 37b is selected [block 2080]. Tangent lines 190, 192 are run along the most distal point 194 and most posterior point 196 of the medial condyle 37b depicted in the selected sagittal MRI image slice 179 [block 2090]. The points 194, 196 serve as the landmark reference points for the medial image 179. The two tangent lines 192, 190 are each parallel to the electronically reoriented Y-Z plane and respectively form axis Y and axis Z. The two tangent lines 190, 192 are generally perpendicular to each other, as indicated in FIG. 18, and intersect at the Y-Z origin, which is set as (Y$_0$, Z$_0$). Therefore, the Y-Z coordinates of the medial condyle 37b are obtained and determined [block 2100].

The Y* axis, Z* axis and origin point (Y*$_0$, Z*$_0$) obtained for the lateral condyle image 178 of FIG. 17 are imported into the medial condyle image 179 [block 2110], as graphically depicted in FIG. 18. Once the Y* axis, Z* axis and origin point (Y*$_0$, Z*$_0$) are properly positioned in the medial image 179 relative to the Y axis, Z axis and origin point (Y$_0$, Z$_0$), the Y axis offset distance $L_Y$ between the Y* axis and the Y axis is measured [block 2120**], and the Z axis offset distance $L_Z$ between the Z* axis and the Z axis is measured [block 2130**].

Figure 19:
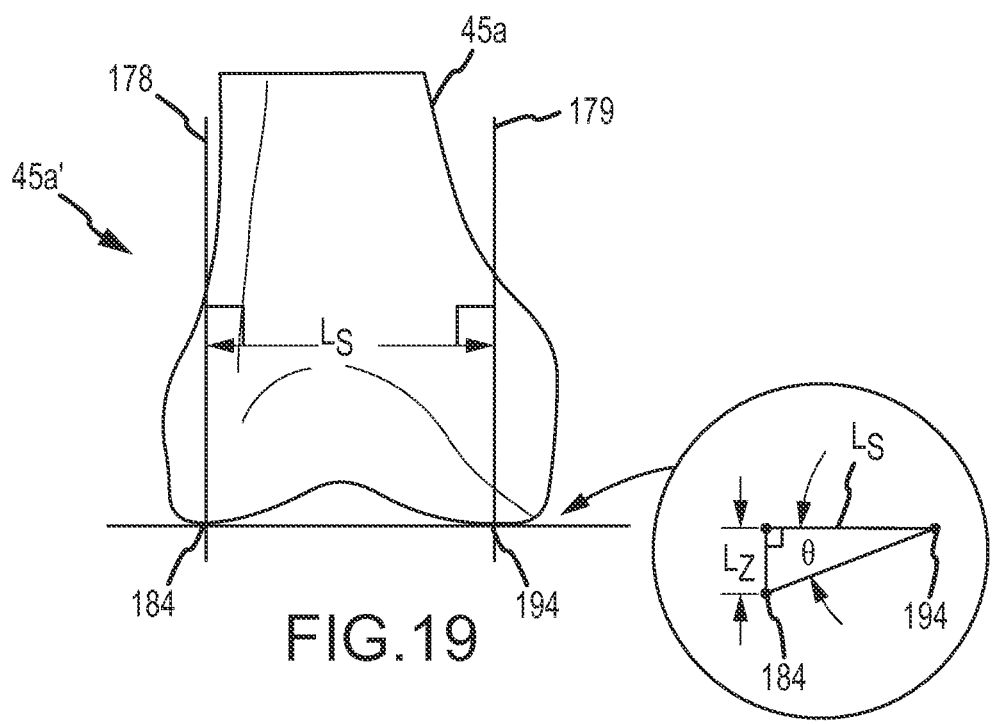
FIGS. 19 and 20 are, respectively, coronal and axial views of the femur with the lateral and medial sagittal MRI image slices of FIGS. 18 and 19 indicated thereon.
Figure 20:
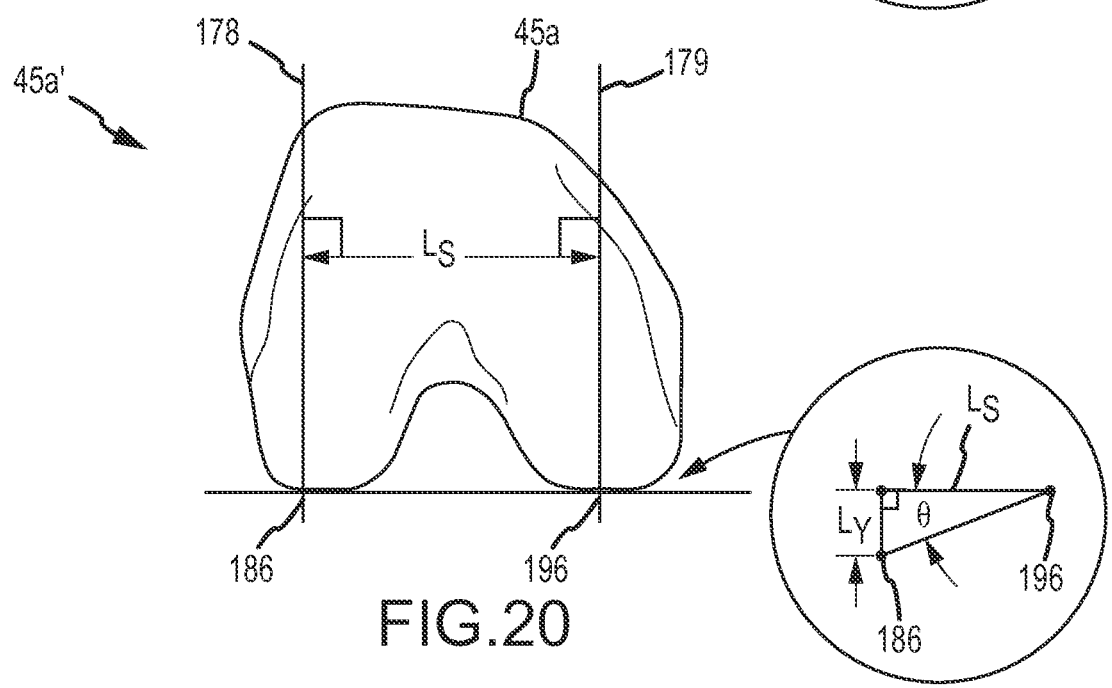

The offset distances $L_Y$ and $L_Z$ are employed in mathematical algorithms to determine whether sagittal MRI image slices 178, 179 are properly electronically reoriented to be readily and reliably useable in creating computer generated 3D bone models [block 2140]. To assist the discussion of the mathematical algorithms, reference is made to FIGS. 19 and 20, which are, respectively, coronal and axial views of the femur 45a with the lateral and medial sagittal MRI image slices 178, 179 of FIGS. 18 and 19 indicated thereon. The mathematical algorithms are as follows: $\theta_y = \arctan L_y/L_S$ and $\theta_z = \arctan L_z/L_S$. As can be understood from FIGS. 18 and 19, $L_S$ is the perpendicular distance between the lateral and medial MRI image slices 178, 179. In other words, $L_S$ is measured perpendicularly to the plane of the sagittal MRI image slices 178, 179. In the context of 2 mm thick sagittal MRI image slices and, for example, there being 20 such slices between sagittal MRI image slices 178, 179, $L_S$ would equal 40 mm.

In one embodiment, if the angles $\theta_y$ and $\theta_z$ are each greater than or equal to −5 degrees and less than or equal to 5 degrees, the sagittal MRI image slices 178, 179 and all other such sagittal image slices are adequately oriented for use in creating computer generated 3D bone models. If the MRI image slices are properly oriented, then the process can proceed to the image motion verification check, which will be discussed next, else the MRI images are rejected and the MRI image orientation and generation procedures must be restarted [block 2150].

Figure 21:
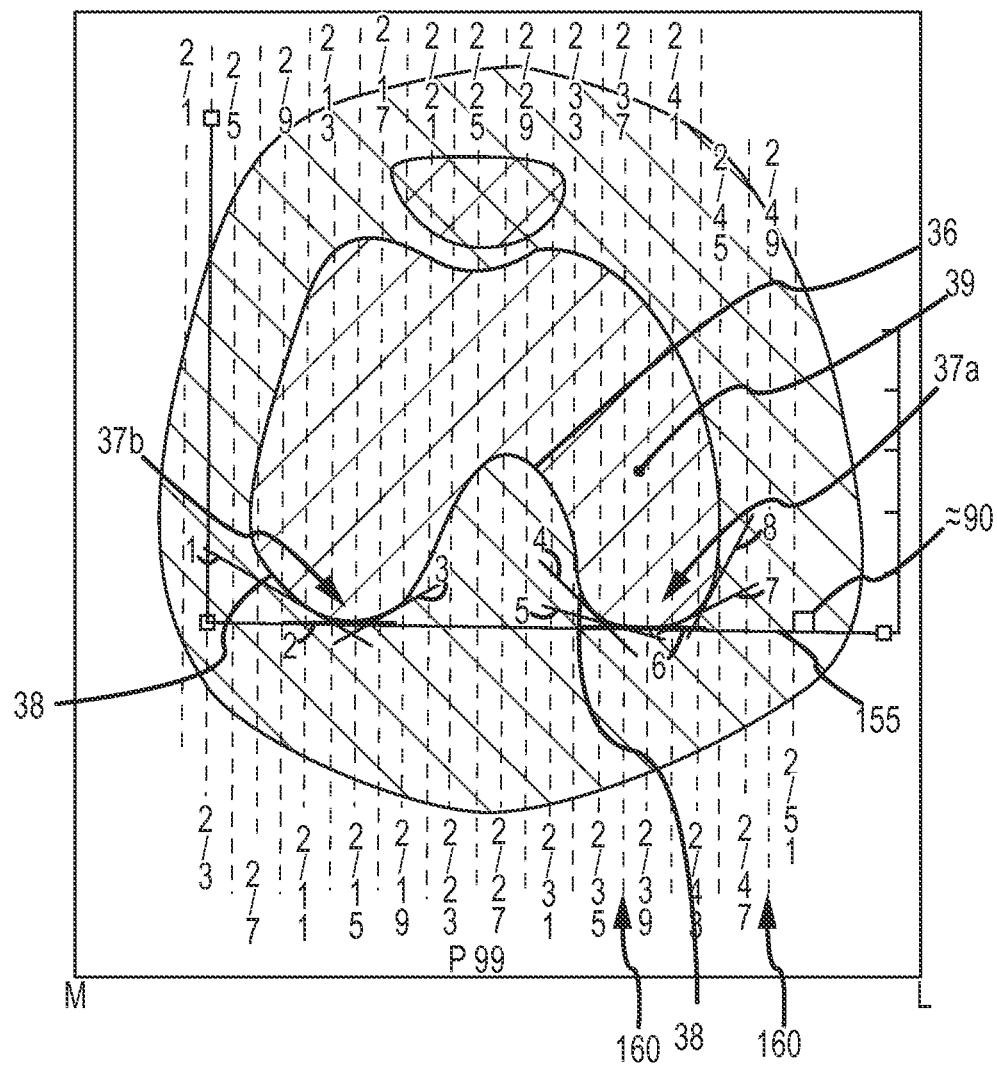
FIG. 21 is an axial MRI image of the distal end of the femur.

For a discussion of the motion verification procedure, reference is made to FIG. 21, which is an axial MRI image of the distal end of the femur. As described above, a series of MRI image slices having, for example, a thickness of 2 mm are generated. The slice planes 160 are indicated in FIG. 21. Depending on the embodiment, the series of image slices may be checked either manually or automatically to determine whether the contours 38 of the slice series follow the contour of the femoral condyles as known in anatomy.

As shown in FIG. 21, the contours 38 of the slice series have a number of tangent lines, which are indicated in FIG. 21 as lines 1, 2, 3, 4, 5, 6, 7, and 8. While eight tangent lines are indicated in FIG. 21, it should be noted that any number of tangent lines may be employed, including numbers greater or less than eight tangent lines.

Moving from medial to lateral, the order of the tangent lines is line-1, line-2, line-3 on the medial condyle 37b and line-4 to line-8 on the lateral condyle 37a. The tangent lines are provided for the purpose of indicating how the tangent slope changes along the contours 38 of the condyles 37.

As depicted in FIG. 21, for the medial condyle 37b, the area from the epicondyle down to the margin of the condyle (the margin is around tangent line-1) shows a steep slope. The volume-averaging data in such an area is not reliable because it shows blurred images with a mix of gray color (cancellous bone or tissue) and black color (cortical bone), where noise is significant. The same analogy applies to the lateral condyle 37a wherein the area laterally outside tangent line-8 has unstable volume-averaging data and high noise.

Returning to the medial condyle 37b, it can be understood that the slopes of the tangent lines reduce from tangent lines-1 to line-2. The slope of the contour in the area of tangent line-2, which is tangent to the lowest extremity of the medial condyle 37b and is generally parallel to the localizer-line 155, is quite stable. Laterally from line-2 the slopes increase from line-2 to line-3. The same slope change pattern can be seen for the lateral condyle 37a from line-4 to line-8. The slopes decrease from line-4 to line 6 and approach constancy in the area of line-6 area, which is tangent to the lowest extremity of the lateral condyle 37a and is generally parallel to the localizer-line 160. The slopes then increase from line-6 to line-8 as the curvature of the lateral condyle 37a increases.

In one embodiment, once the tangent lines are determined [block 2160], the slope data of the tangent lines can be recorded [block 2170]. For example, the slopes are a maximum negative value around line-1, the slopes are close to zero or constant around line-2, and the slopes are a maximum positive value around line-3. Based on the slope information, each slice in a series order can be checked to determine if an up/down motion occurred during the generation of the MRI image slices [block 2180]. If one or more slices do not follow the normal slope change pattern (e.g., the one or more slices are outside or inside the slope pattern), then motion has been detected. The motion may be the result of patient movement during the MRI scan. If the image motion is sufficiently negligible (e.g., less than or equal to 1 mm), then provide the generated MRI image slices to the 3D modeling program at the CPU 50 (i.e., go to [block 1040] of FIG. 1), else reject the MRI images and start the MRI image orientation and generation procedure over (i.e., return to [block 2000]) [block 2190]. In other words, where the detected motion is less than or equal to 1 mm, the MRI image data is transferred to computer image programs, as disclosed in: (1) Park et al., U.S. patent application Ser. No. 11/641,569, filed on Jan. 19, 2007, a continuation of U.S. patent application Ser. No. 10/146,862, filed on May 15, 2002; (2) U.S. patent application Ser. No. 11/656,323, filed on Jan. 19, 2007; and (3) Park et al., U.S. patent application Ser. No. 11/642,385, filed on Dec. 19, 2006. Each of these patent applications is incorporated by reference into this Detailed Description in its entirety.

In one embodiment as an additional or alternative method of detecting motion, the femur condyle contour shapes of at least some, if not all, MRI image slices are compared to contours of femur condyles known to be healthy and properly formed. Such anatomically correct contours of healthy and properly formed femur condyles may be obtained from a database containing such contours from medical studies and/or libraries. Motion may be detected where one or more of the femur condyle contours of the MRI do not adequately correspond to the anatomically correct condyle contours. The comparison of the MRI contours to the anatomically correct contours may be done either manually or automatically, depending on the embodiment.

The following discussion provides a summary of one embodiment of a method for generating 2D MRI images that are readily and reliably useable to create computer generated 3D bone models usable for manufacturing customized arthroplasty bone jigs.

General Positioning. A dedicated extremity coil (e.g., knee coil, ankle coil, elbow coil, neck coil, etc.) is selected. The extremity (e.g., knee, ankle, elbow, neck, etc.) is centered in the coil in a position of comfort. Sponges may be placed around the extremity within the coil to center the extremity in the coil. The patient is instructed to remain absolutely still during the MRI scanning process, because, in some embodiments, a movement of 1 mm or more may cause rejection of the MRI scan.

MRI Set-up. The patient's name, birth date, and age are entered. The extremity to be scanned is identified (e.g., right or left knee). The surgeon's name, the imaging center's name and the scan date are entered.

Three-plane Locator. A slice thickness of 4 mm is selected, wherein two spatially offset runs are to be made at 4 mm and then combined to achieve a slice spacing of 2 mm. Additional setting parameters include: field of view ("FOV") equals 20-24 cm; higher matrix 256×256 or hi-res; number of excitations ("NEX") equals 2 or higher; and seven slices in each plane. Parameters for the 3-plane locator are adjustable. The images are to be made as clear as possible, which allows for better visualization of the cortical-cancellous edges used for alignment. The image may be magnified or zoomed when aligning the sagittal scan slices, which helps to get the scan slices perpendicular to the cortical-cancellous bone.

Alignment For Sagittal Images. Using the best axial image from the 3-plane locator, adjust the sagittal slices until they are perpendicular to the cortical-cancellous edge of the posterior femur condyles (see FIG. 16). Alternatively or additionally, using the best coronal image from the 3-plane locator, adjust the sagittal slices to until they are perpendicular to the cortical-cancellous edge of the inferior femur condyles (see FIG. 15). Preferably, at least two slices should be obtained beyond the femur condylar and tibial medial/lateral margins. All bony anatomy should be included.

In one embodiment, the MRI technician places the 3D localizer lines 150, 150 on the cortical-cancellous edge 38 of the femur to set-up sagittal slice planes that are at least roughly properly oriented for purposes of generating computer generated 3D bone models. The proper orientation of the sagittal slice planes is then verified via the verification process discussed with respect to FIGS. 17-20.

In some embodiments, the 3D localizer lines 150, 155 may be located on similar cortical-cancellous edges of the tibia to electronically orient the femur and/or tibia. However, in some embodiments, it is preferred to simply rely on placing the localizer lines 150, 155 on the cortical-cancellous edges of the femur condyle features because in many cases the tibia plateau is worn out in one side or two sides, making it hard to provide joint line information via the tibia. Since the exact location of the joint line is unknown, but the localizer lines 150, 155, when applied to the cortical/cancellous edges of the femur condyles as discussed above, can be assumed to be generally parallel to the joint line, the MRI technician is instructed to apply the localizers lines as discussed above.

The localizer lines 150, 155 can be applied to the features of the femur condyles both in a knee with 90-degree extension (the axial view in FIG. 16) and/or in a knee with zero-degree extension (the coronal view in FIG. 15). In one embodiment, the adequacy of the electronic orientation of the generated MRI sagittal slices is generally unknown at this point. Consequently, verifications are made regarding the alignment of the sagittal images and whether motion was present during the MRI scanning process.

Scan Sequence Quality Check. Check scan sequence before removing patient from scanner. Repeat the scanning if motion or mis-alignment is noted.

Alignment Check. Based on the information from coronal view and the axial view, check the offset between two the medial and lateral femur condyles and measure the angle by the algorithm, as discussed with respect to FIGS. 17-20. If the angles are equal to or greater than 5 degrees or equal to or less than −5 degrees, then the images are rejected and a MRI rescan is required. If the angle is within or equal to between 5 degrees and −5 degrees, then the motion check is performed.

Motion check: Motion can be checked for either manually or automatically by checking either the slope change information (as can be understood from the discussion regarding FIG. 21) or via slice-by-slice contour shape changes that follow real anatomical contours of femur condyles. With respect to the real anatomical contours of femur condyles, such anatomical contours may be those provided via a medical library of healthy, normally formed femur condyles.

Motion may be detected by a subtle movement or slight jumping from one image acquisition to another. Jumping can be seen in sagittal or coronal views. If motion is detected, repeat scan; do not upload or otherwise use image with motion.

Repeat the scanning if grainy images, FOV is off, or entire bone areas of interest are not visualized. For grainy images, poor signal to noise ratio ("SNR"), check parameters and adjust. For the FOV, the amount of femur and tibia should be the same, wherein FOV is approximately 16 cm. If the entire femur medial/lateral condyle is not visualized, adjust image.

When To Perform A CT Arthrogram. Perform a CR arthrogram instead of a MRI when: the dedicated extremity coil does not fit around the extremity to be scanned; when there is a hardware or ferromagnetic artifact; the patient cannot hold still due to pain, tremor, or cannot follow instructions due to dementia, stroke, etc.; or the patient has a pacemaker or any other contradictions.

The system and method disclosed herein for making customized arthroplasty jigs 20 is beneficial because they substantially reduce both the time associated with generating acceptable 2D MRI image slices 10 and the likelihood of having to repeat the MRI process. As a result, MRI costs, in terms of money and patient stress, are substantially reduced. Additionally, lead-time is substantially reduced for arthroplasty procedures utilizing customized arthroplasty jigs. These benefits are made possible, at least in part, by the image resolutions, the image slice spacings, and the image orientation methods disclosed herein.

Although the present invention has been described with reference to preferred embodiments, persons skilled in the art will recognize that changes may be made in form and detail without departing from the spirit and scope of the invention.

What is claimed is:

1. A method of modeling a patient's joint area, the method comprising:

obtaining two-dimensional MRI images of the patient's joint area, the two-dimensional MRI images including coronal, axial, and sagittal MRI images;

identifying a first pair of boney landmarks in the axial MRI images;

connecting the first pair of boney landmarks with a first tangent line;

identifying a second pair of boney landmarks in the coronal MRI images;

connecting the second pair of boney landmarks with a second tangent line;

subsequent to obtaining the two-dimensional MRI images, electronically reorienting the sagittal MRI images to account for the patient's joint area being randomly physically oriented in a scanning area of a MRI machine by adjusting an orientation of the sagittal MRI images to be: perpendicular to the first tangent line connecting the first pair of boney landmarks in the axial MRI images; and perpendicular to the second tangent line connecting the second pair of boney landmarks in the coronal MRI images;

verifying the electronically reoriented sagittal MRI images are properly oriented in a first and a second operation, the first operation comprising utilizing a first offset distance between a first most distal point on a medial femoral condyle and a second most distal point on a lateral femoral condyle, the second operation comprising utilizing a second offset distance between a first most posterior point on a medial femoral condyle and a second most posterior point on a lateral femoral condyle, wherein, in the first operation, verifying the electronically reoriented sagittal MRI images are properly oriented further comprises electronically computing a first angle defined as arctangent of a fraction defined as the first offset distance divided by a first perpendicular distance between the first sagittal MRI image and the second sagittal MRI image, wherein, in the first operation, the electronically reoriented sagittal MRI images are properly oriented when the first angle is greater than or equal to minus 5 degrees and less than or equal to five degrees; and using a computer to generate a three-dimensional bone image of at least a portion of a bone of the patient's joint area from the electronically reoriented sagittal MRI images.

2. A method of modeling a patient's joint area, the method comprising:

obtaining two-dimensional MRI images of the patient's joint area, the two-dimensional MRI images including coronal, axial, and sagittal MRI images;

identifying a first pair of boney landmarks in the axial MRI images;

connecting the first pair of boney landmarks with a first tangent line;

identifying a second pair of boney landmarks in the coronal MRI images;

connecting the second pair of boney landmarks with a second tangent line;

subsequent to obtaining the two-dimensional MRI images, electronically reorienting the sagittal MRI images to account for the patient's joint area being randomly physically oriented in a scanning area of a MRI machine by adjusting an orientation of the sagittal MRI images to be: perpendicular to the first tangent line connecting the first pair of boney landmarks in the axial MRI images; and perpendicular to the second tangent line connecting the second pair of boney landmarks in the coronal MRI images;

verifying the electronically reoriented sagittal MRI images are properly oriented in a first and a second operation, the first operation comprising utilizing a first offset distance between a first most distal point on a medial femoral condyle and a second most distal point on a lateral femoral condyle, the second operation comprising utilizing a second offset distance between a first most posterior point on a medial femoral condyle and a second most posterior point on a lateral femoral condyle, wherein the first most posterior point on the medial femoral condyle is depicted in a first sagittal MRI image of the electronically reoriented sagittal MRI images depicting a largest cross section of the medial femoral condyle, and wherein the second most posterior point on the lateral femoral condyle is depicted in a second sagittal MRI image of the electronically reoriented sagittal MRI images depicting a largest cross section of the lateral femoral condyle, wherein, in the second operation, verifying the electronically reoriented sagittal MRI images are properly oriented further comprises electronically computing a second angle defined as arctangent of a fraction defined as the second offset distance divided by a second perpendicular distance between the first sagittal MRI image and the second sagittal MRI image, wherein, in the second operation, the electronically reoriented sagittal MRI images are properly oriented when the second angle is greater than or equal to minus 5 degrees and less than or equal to five degrees; and using a computer to generate a three-dimensional bone image of at least a portion of a bone of the patient's joint area from the electronically reoriented sagittal MRI images.

* * * * *